(12) United States Patent
Min

(10) Patent No.: US 10,588,946 B2
(45) Date of Patent: Mar. 17, 2020

(54) PEPTIDE FOR PROMOTING BONE FORMATION OR INHIBITING BONE RESORPTION AND USE THEREOF

(71) Applicant: SEOUL NATIONAL UNIVERSITY R&DB FOUNDATION, Seoul (KR)

(72) Inventor: Byung Moo Min, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 0 days.

(21) Appl. No.: 15/737,593

(22) PCT Filed: Jun. 17, 2016

(86) PCT No.: PCT/KR2016/006430
§ 371 (c)(1),
(2) Date: Dec. 18, 2017

(87) PCT Pub. No.: WO2016/204545
PCT Pub. Date: Dec. 22, 2016

(65) Prior Publication Data
US 2018/0193428 A1    Jul. 12, 2018

(30) Foreign Application Priority Data
Jun. 18, 2015 (KR) .................. 10-2015-0086779

(51) Int. Cl.
| | | |
|---|---|---|
| *A61K 38/39* | (2006.01) | |
| *A61K 38/10* | (2006.01) | |
| *C07K 14/78* | (2006.01) | |
| *C07K 7/08* | (2006.01) | |
| *A61P 19/08* | (2006.01) | |
| *C12N 15/63* | (2006.01) | |
| *A61K 38/08* | (2019.01) | |
| *A61K 48/00* | (2006.01) | |
| *A61P 1/02* | (2006.01) | |
| *A61P 19/02* | (2006.01) | |
| *A61P 19/10* | (2006.01) | |

(52) U.S. Cl.
CPC .............. *A61K 38/39* (2013.01); *A61K 38/08* (2013.01); *A61K 38/10* (2013.01); *A61K 48/00* (2013.01); *A61P 1/02* (2018.01); *A61P 19/02* (2018.01); *A61P 19/10* (2018.01); *C07K 7/08* (2013.01); *C07K 14/78* (2013.01); *C12N 15/63* (2013.01)

(58) Field of Classification Search
None
See application file for complete search history.

(56) References Cited

U.S. PATENT DOCUMENTS

| | | | |
|---|---|---|---|
| 5,849,865 A | 12/1998 | Cheng et al. | |
| 8,728,509 B2 * | 5/2014 | McKay ................. | A61L 27/227 424/422 |
| 2005/0147645 A1 * | 7/2005 | Budny ................... | A61L 27/02 424/423 |
| 2012/0301962 A1 | 11/2012 | Thomson et al. | |

FOREIGN PATENT DOCUMENTS

| | | |
|---|---|---|
| KR | 10-2006-0118447 A | 11/2006 |
| KR | 10-2012-0105248 A | 9/2012 |
| WO | 2005/087809 A2 | 9/2005 |

OTHER PUBLICATIONS

Kirsch et al., EMBO J., 2000, 19(13):3314-3324.*
Perlin et al., Soft Matter, 2008, vol. 4:2331-2349.*
International Search Report and Written Opinion dated Sep. 27, 2016 from International Application No. PCT/KR2016/006430, 13 pages with English translation.
NCBI, "Vitronectin [*Homo sapiens*]", GenBank Accession No. AAH05046.1, Definition; Origin,Jul. 15, 2006, 2 pages.
Salasznyk et al., "Adhesion to Vitronectin and Collagen I Promotes Osteogenic Differentiation of Human Mesenchymal Stem Cells", Journal of Biomedicine and Biotechnology, 2004, vol. 2004, Issue 1, pp. 24-34.
Zhang et al., "Bioactive Coatings for Orthopaedic Implants—Recent Trends in Development of Implant Coatings", International Journal of Molecular Sciences, 2014, vol. 15, pp. 11878-11921.
Yeo et al., "Collagen-Based Biomimetic Nanofibrous Scaffolds: Preparation and Characterization of Collagen/Silk Fibroin Bicomponent Nanofibrous Structures", Biomacromolecules, 2008, vol. 9, pp. 1106-1116.
Min et al., "Electrospinning of silk fibroin nanofibers and its effect on the adhesion and spreading of normal human keratinocytes and fibroblasts in vitro", Biomaterials, 2004, vol. 25, pp. 1289-1297.
Lee et al., "Trolox Prevents Osteoclastogenesis by Suppressing RANKL Expression and Signaling", The Journal of Biological Chemistry, May 15, 2009, vol. 284, No. 20, pp. 13725-13734.
Lee et al., "The induction of bone formation in rat calvarial defects and subcutaneous tissues by recombinant human BMP-2, produced in *Escherichia coli*", Biomaterials, 2010, vol. 31, pp. 3512-3519.
Kim et al., "The PPFLMLLKGSTR motif in globular domain 3 of the human laminin-5 α3 chain is crucial for integrin α3β1 binding and cell adhesion", Experimental Cell Research, 2005, vol. 304, pp. 317-327.

(Continued)

*Primary Examiner* — Xiaozhen Xie
(74) *Attorney, Agent, or Firm* — MH2 Technology Law Group, LLP

(57) ABSTRACT

The present invention relates to a peptide for promoting bone formation or inhibiting bone resorption and use thereof. The peptide for regulating bone formation or bone resorption of the present invention has the effect of promoting bone formation by enhancing osteoblast differentiation and concurrently inhibiting bone resorption by restricting osteoclast differentiation and resorptive function. Additionally, due to the low molecular weight, the peptide can be economically produced, and is thus useful for preventing and treating bone diseases.

11 Claims, 34 Drawing Sheets

Specification includes a Sequence Listing.

(56) References Cited

OTHER PUBLICATIONS

Kamikubo et al., "Identification of the Disulfide Bonds in the Recombinant Somatomedin B Domain of Human Vitronectin", The Journal of Biological Chemistry, Jul. 26, 2002, vol. 277, No. 30, pp. 27109-27119.
Notice of Allowance dated Aug. 24, 2018 for Korean Patent Application No. KR20160075873, 4 pages.
NCBI , "Predicted: Vitronectin [*Colobus angolensis palliatus*]", NCBI Reference Sequence: XP_011796165.1, Mar. 30, 2015, 2 pages.
Min et al., "Effect of bio-active ECM peptides on tissue regeneration", Final report of Middle-aged Researcher Support Project (Core Research), Basic Business Research, Ministry of Education and Science Technology, 2013, Department of Dentistry, Seoul National University School of Dentistry, Apr. 5, 2013, 80 pages, with English summary (see p. 5).

\* cited by examiner

SEQUENCE LISTING

```
<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: forward primer for ALP

<400> SEQUENCE: 1
cccacgtcga ttgcatctct                                                   20

<210> SEQ ID NO 2
<211> LENGTH: 20
<212> TYPE: DNA
<213> ORGANISM: Artificial Sequence
<220> FEATURE:
<223> OTHER INFORMATION: reverse primer for ALP

<400> SEQUENCE: 2
agtaaggcag gtgccaatgg                                                   20

<210> SEQ ID NO 3
<211> LENGTH: 19
<212> TYPE: DNA
<213> ORGANISM: Artificial Sequence
<220> FEATURE:
<223> OTHER INFORMATION: forward primer for UNX2

<400> SEQUENCE: 3
gccttcaagg tggtagccc                                                    19

<210> SEQ ID NO 4
<211> LENGTH: 20
<212> TYPE: DNA
<213> ORGANISM: Artificial Sequence
<220> FEATURE:
<223> OTHER INFORMATION: reverse primer for UNX2

<400> SEQUENCE: 4
cgttacccgc catgacagta                                                   20

<210> SEQ ID NO 5
<211> LENGTH: 23
<212> TYPE: DNA
<213> ORGANISM: Artificial Sequence
<220> FEATURE:
<223> OTHER INFORMATION: forward primer for Bone sialoprotein

<400> SEQUENCE: 5
aaggctacga tggctatgat ggt                                               23

<210> SEQ ID NO 6
```

```
<211> LENGTH: 20
<212> TYPE: DNA
<213> ORGANISM: Artificial Sequence
<220> FEATURE:
<223> OTHER INFORMATION: reverse primer for Bone sialoprotein

<400> SEQUENCE: 6
aatggtagcc ggatgcaaag                                                   20

<210> SEQ ID NO 7
<211> LENGTH: 16
<212> TYPE: DNA
<213> ORGANISM: Artificial Sequence
<220> FEATURE:
<223> OTHER INFORMATION: forward primer for Osteocalcin

<400> SEQUENCE: 7
gaagcccagc ggtgca                                                       16

<210> SEQ ID NO 8
<211> LENGTH: 19
<212> TYPE: DNA
<213> ORGANISM: Artificial Sequence
<220> FEATURE:
<223> OTHER INFORMATION: reverse primer for Osteocalcin

<400> SEQUENCE: 8
cactacctcg ctgccctcc                                                    19

<210> SEQ ID NO 9
<211> LENGTH: 21
<212> TYPE: DNA
<213> ORGANISM: Artificial Sequence
<220> FEATURE:
<223> OTHER INFORMATION: forward primer for GAPDH

<400> SEQUENCE: 9
ccatcttcca ggagcgagat c                                                 21

<210> SEQ ID NO 10
<211> LENGTH: 20
<212> TYPE: DNA
<213> ORGANISM: Artificial Sequence
<220> FEATURE:
<223> OTHER INFORMATION: reverse primer for GAPDH

<400> SEQUENCE: 10
gccttctcca tggtggtgaa                                                   20

<210> SEQ ID NO 11
<211> LENGTH: 24
<212> TYPE: DNA
<213> ORGANISM: Artificial Sequence
<220> FEATURE:
<223> OTHER INFORMATION: sense primer for Vn-FI

<400> SEQUENCE: 11
ggatccgacc aagagtcatg caag                                              24

<210> SEQ ID NO 12
<211> LENGTH: 23
<212> TYPE: DNA
<213> ORGANISM: Artificial Sequence
<220> FEATURE:
<223> OTHER INFORMATION: antisense primer for Vn-FI

<400> SEQUENCE: 12
```

```
gaattctcag ggctgaggtc tcc                                          23
```

<210> SEQ ID NO 13
<211> LENGTH: 22
<212> TYPE: DNA
<213> ORGANISM: Artificial Sequence
<220> FEATURE:
<223> OTHER INFORMATION: sense primer for Vn-FII

<400> SEQUENCE: 13

```
ggatccccag cagaggagga gc                                           22
```

<210> SEQ ID NO 14
<211> LENGTH: 28
<212> TYPE: DNA
<213> ORGANISM: Artificial Sequence
<220> FEATURE:
<223> OTHER INFORMATION: antisense primer for Vn-FII

<400> SEQUENCE: 14

```
gaattctcac cagaagagaa gctcgaag                                     28
```

<210> SEQ ID NO 15
<211> LENGTH: 19
<212> TYPE: DNA
<213> ORGANISM: Artificial Sequence
<220> FEATURE:
<223> OTHER INFORMATION: sense primer for Vn-FIII

<400> SEQUENCE: 15

```
ggatccggca gaacctctg                                               19
```

<210> SEQ ID NO 16
<211> LENGTH: 26
<212> TYPE: DNA
<213> ORGANISM: Artificial Sequence
<220> FEATURE:
<223> OTHER INFORMATION: antisense primer for Vn-FIII

<400> SEQUENCE: 16

```
gaattctcac agatggccag gagctg                                       26
```

<210> SEQ ID NO 17
<211> LENGTH: 12
<212> TYPE: PRT
<213> ORGANISM: Artificial Sequence
<220> FEATURE:
<223> OTHER INFORMATION: VnP-16

<400> SEQUENCE: 17

Arg Val Tyr Phe Phe Lys Gly Lys Gln Tyr Trp Glu
1               5                   10

<210> SEQ ID NO 18
<211> LENGTH: 130
<212> TYPE: PRT
<213> ORGANISM: Artificial Sequence
<220> FEATURE:
<223> OTHER INFORMATION: rVn-FI

<400> SEQUENCE: 18

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

```
Thr Asp Tyr Thr Ala Glu Cys Lys Pro Gln Val Thr Arg Gly Asp Val
             35                  40                  45

Phe Thr Met Pro Glu Asp Glu Tyr Thr Val Tyr Asp Asp Gly Glu Glu
 50                  55                  60

Lys Asn Asn Ala Thr Val His Glu Gln Val Gly Gly Pro Ser Leu Thr
 65                  70                  75                  80

Ser Asp Leu Gln Ala Gln Ser Lys Gly Asn Pro Glu Gln Thr Pro Val
             85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
            115                 120                 125

Gln Pro
    130

<210> SEQ ID NO 19
<211> LENGTH: 173
<212> TYPE: PRT
<213> ORGANISM: Artificial Sequence
<220> FEATURE:
<223> OTHER INFORMATION: rVn-FII

<400> SEQUENCE: 19

Pro Ala Glu Glu Glu Leu Cys Ser Gly Lys Pro Phe Asp Ala Phe Thr
 1               5                  10                  15

Asp Leu Lys Asn Gly Ser Leu Phe Ala Phe Arg Gly Gln Tyr Cys Tyr
             20                  25                  30

Glu Leu Asp Glu Lys Ala Val Arg Pro Gly Tyr Pro Lys Leu Ile Arg
             35                  40                  45

Asp Val Trp Gly Ile Glu Gly Pro Ile Asp Ala Ala Phe Thr Arg Ile
 50                  55                  60

Asn Cys Gln Gly Lys Thr Tyr Leu Phe Lys Gly Ser Gln Tyr Trp Arg
 65                  70                  75                  80

Phe Glu Asp Gly Val Leu Asp Pro Asp Tyr Pro Arg Asn Ile Ser Asp
             85                  90                  95

Gly Phe Asp Gly Ile Pro Asp Asn Val Asp Ala Ala Leu Ala Leu Pro
            100                 105                 110

Ala His Ser Tyr Ser Gly Arg Glu Arg Val Tyr Phe Phe Lys Gly Lys
            115                 120                 125

Gln Tyr Trp Glu Tyr Gln Phe Gln His Gln Pro Ser Gln Glu Glu Cys
    130                 135                 140

Glu Gly Ser Ser Leu Ser Ala Val Phe Glu His Phe Ala Met Met Gln
145                 150                 155                 160

Arg Asp Ser Trp Glu Asp Ile Phe Glu Leu Leu Phe Trp
                165                 170

<210> SEQ ID NO 20
<211> LENGTH: 156
<212> TYPE: PRT
<213> ORGANISM: Artificial Sequence
<220> FEATURE:
<223> OTHER INFORMATION: rVn-FIII

<400> SEQUENCE: 20

Gly Arg Thr Ser Ala Gly Thr Arg Gln Pro Gln Phe Ile Ser Arg Asp
 1               5                  10                  15

Trp His Gly Val Pro Gly Gln Val Asp Ala Ala Met Ala Gly Arg Ile
```

```
                    20              25              30
Tyr Ile Ser Gly Met Ala Pro Arg Pro Ser Leu Ala Lys Lys Gln Arg
        35              40              45

Phe Arg His Arg Asn Arg Lys Gly Tyr Arg Ser Gln Arg Gly His Ser
    50              55              60

Arg Gly Arg Asn Gln Asn Ser Arg Arg Pro Ser Arg Ala Thr Trp Leu
65              70              75              80

Ser Leu Phe Ser Ser Glu Glu Ser Asn Leu Gly Ala Asn Asn Tyr Asp
            85              90              95

Asp Tyr Arg Met Asp Trp Leu Val Pro Ala Thr Cys Glu Pro Ile Gln
                100             105             110

Ser Val Phe Phe Ser Gly Asp Lys Tyr Tyr Arg Val Asn Leu Arg
        115             120             125

Thr Arg Arg Val Asp Thr Val Asp Pro Pro Tyr Pro Arg Ser Ile Ala
    130             135             140

Gln Tyr Trp Leu Gly Cys Pro Ala Pro Gly His Leu
145             150             155

<210> SEQ ID NO 21
<211> LENGTH: 12
<212> TYPE: PRT
<213> ORGANISM: Artificial Sequence
<220> FEATURE:
<223> OTHER INFORMATION: VnP-15

<400> SEQUENCE: 21

Ala His Ser Tyr Ser Gly Arg Glu Arg Val Tyr Phe
1               5                   10

<210> SEQ ID NO 22
<211> LENGTH: 12
<212> TYPE: PRT
<213> ORGANISM: Artificial Sequence
<220> FEATURE:
<223> OTHER INFORMATION: VnP-17

<400> SEQUENCE: 22

Gln Tyr Trp Glu Tyr Gln Phe Gln His Gln Pro Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Scrambled peptide

<400> SEQUENCE: 23

Phe Val Trp Arg Gln Phe Tyr Lys Tyr Glu Lys Gly
1               5                   10
```

PEPTIDE FOR PROMOTING BONE FORMATION OR INHIBITING BONE RESORPTION AND USE THEREOF

CROSS-REFERENCE TO RELATED APPLICATIONS

This application is a U.S. National Stage application of PCT/KR2016/006430 filed 17 Jun. 2016, which claims the benefit of, and relies on the filing date of, Korean Patent Application No. 10-2015-0086779, filed 18 Jun. 2015, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on 3 Sep. 2019, is named 0312_0002-US Sequence Listing.txt and is 9 Kilobytes in size.

TECHNICAL FIELD

The present invention relates to a peptide for promoting bone formation or inhibiting bone resorption and use thereof.

BACKGROUND ART

Bone defects that may result from fractures, accidents, cancer, or other diseases can pose a serious risk of loss of bone function, and thereby impair the quality of life. Tissue grafting methods, etc. are currently used for the treatment of bone diseases, but these methods still have limitations such as donor site morbidity and graft rejection.

Meanwhile, due to the flexibility in selecting and mimicking the local structural features of proteins, peptides can functionally serve as valid alternatives to entire proteins. Peptides have advantages in that they have a low molecular weight, synthetic versatility, and economical production. The use of peptides in regenerative medicine has advantages over the use of entire proteins in terms of lowering immunogenicity, susceptibility to protein degradation, tumor-related side effects, etc., and is superior in terms of drug targeting, drug potency, stability, and bioavailability compared to those of other protein-based biological therapeutics. Until now, many peptides have been used for local applications to repair bone defects in clinical settings; however, only very few peptides were shown to have the ability to form bone themselves, and these peptides also have many disadvantages in that the use thereof for therapeutics is associated with high cost, etc.

Meanwhile, bone mass and structure are maintained through a dynamic balance between bone resorption and formation. An imbalance caused by the increased activity and/or number of osteoclasts leads to bone destruction in pathological bone diseases, including osteoporosis, Paget's disease, rheumatoid arthritis, osteolytic metastases, etc. Therefore, much attention has been focused on the pharmacological control of osteoclasts for the treatment of osteoclast-related bone disorders including osteoporosis and arthritis.

DISCLOSURE

Technical Problem

The present inventors have made many efforts to develop a therapeutic agent for the treatment of bone diseases, which can regulate both bone formation and bone resorption. As a result, the present inventors have developed an RVYFFK-GKQYWE (SEQ ID NO: 17) motif (VnP-16) present within human vitronectin capable of promoting the activity and differentiation of osteoblasts through β1 integrin by inducing the activation of focal adhesion kinase (FAK). Additionally, the present inventors have confirmed that VnP-16 can promote bone formation by enhancing osteoblast differentiation both in vitro and in vivo while concurrently restricting bone resorption by inhibiting osteoblast differentiation and resorptive function, thereby completing the present invention.

Technical Solution

An object of the present invention is to provide a peptide for regulating bone formation or bone resorption, which consists of 12 to 173 continuous amino acids containing the amino acid sequence (RVYFFKGKQYWE) of SEQ ID NO: 17 within the amino acid sequence of SEQ ID NO: 19.

Another object of the present invention is to provide a peptide for regulating bone formation or bone resorption containing the amino acid sequence (RVYFFKGKQYWE) of SEQ ID NO: 17.

Still another object of the present invention is to provide a polynucleotide encoding the peptide.

Still another object of the present invention is to provide a recombinant vector containing the polynucleotide.

Still another object of the present invention is to provide a pharmaceutical composition for preventing or treating bone disease, which contains the peptide, a polynucleotide encoding the peptide, or a recombinant vector containing the polynucleotide as an active ingredient.

Advantageous Effects of the Invention

The peptide for regulating bone formation or bone resorption of the present invention has effects of promoting osteoblast differentiation while simultaneously promoting bone formation by restricting bone resorption by inhibiting osteoclast differentiation and resorptive function. Additionally, due to the low molecular weight, the peptide can be economically produced, and thus is useful for preventing and treating bone diseases.

BRIEF DESCRIPTION OF DRAWINGS

FIG. 1a shows a partial amino acid sequence alignment of the central region of human vitronectin (amino acids at positions 230 to 322).

FIG. 1b shows the results of cells which were dose-dependently attached to synthetic peptides immobilized on plates. Human osteoblasts were allowed to adhere onto peptide-coated plates for 1 hour in serum-free medium.

FIGS. 1c and 1d show the results with regard to (c) attachment and (d) spreading of osteogenic cells induced for 1 hour (c) and 3 hours (d) by treatment with BSA (1%), vitronectin (0.23 µg/cm$^2$), rVn-FII (5.7 µg/cm$^2$), and synthetic peptides (9.1 µg/cm$^2$) in serum-free medium.

FIG. 1e shows the results of viability tests performed using the water-soluble tetrazolium salt method for osteogenic cells, NHDFs, NHOFs, MC3T3-E1, and NIH/3T3 cells treated with VnP-16 for 24 hours and 48 hours.

FIG. 1f shows the results with regard to the attachment of NHEKs, NHOKs, NHDFs, NHOFs, PC-12, MC3T3-E1, CV-1, and NIH/3T3 cells to VnP-16. Osteogenic cells were allowed to adhere onto the plates precoated with VnP-16 (9.1 μg/cm$^2$) in serum-free medium for 1 hour.

FIG. 1g shows the predicted structure of the VnP-16 dodecapeptide computed using the PSIPRED protein structure prediction server (*P<0.01). The results are expressed as mean±S.D. (n=4).

FIG. 2a shows the results with regard to the attachment of human osteogenic cells, which were cultured in plates precoated with VnP-16 (9.1 μg/cm$^2$) for 1 hour, to VnP-16. The human osteogenic cells were treated with EDTA (5 mM), MnCl$_2$ (500 μM), or heparin (100 μg/mL) to VnP-16, respectively.

FIG. 2b shows the results with regard to the attachment of cells, which were completely blocked by the treatment with β1 integrin-blocking antibodies, to VnP-16 (mean±S.D., n=3).

FIGS. 2c and 2d show the results of an immunoblot analysis (c) of β1 integrin and cell attachment to VnP-16 (mean±S.D., n=4) (d) in osteogenic cells that were transfected with a control (Con) siRNA (10 nM) or β1 integrin siRNA (10 nM).

FIG. 2e shows the results of a pulldown assay performed using a biotinylated VnP-16 peptide or streptavidin-bead alone, to confirm whether VnP-16 directly binds to β1 integrin. Human osteogenic cells or HOS cells that were cultured for 3 hours in biotinylated VnP-16-coated dishes, in which β1 integrin was present on their surface, were used for the assay.

FIG. 2f shows the results of an immunoblot analysis of the phospho-acceptor sites in FAK, phospho-Akt Ser473, phospho-PKCδ Thr505, and phospho-c-Src Tyr416 from osteogenic cells cultured for 3 hours on plates coated with vitronectin (0.23 μg/cm$^2$), scrambled peptide (SP), or VnP-16 (9.1 μg/cm$^2$).

FIG. 2g shows the results of an immunoblot analysis of phospho-FAK Tyr397 in osteogenic cells pretreated with PF-573228, a FAK inhibitor, for 1 hour.

FIG. 2h shows the results of cell attachment to VnP-16 in the PF-573228-treated cells for 1 hour. The cells were seeded on plates precoated with VnP-16 (9.1 μg/cm$^2$) for 1 hour in serum-free medium (mean±S.D., n=4).

FIG. 2i shows images which confirm that PF-573228 inhibits differentiation of osteogenic cells. SKP-derived mesenchymal cells (MSCs), mouse calvarial osteoblast precursors (MC3T3-E1), and human osteogenic cells (Osteogenic) were cultured on VnP-16 (9.1 μg/cm$^2$)-coated plates in osteogenic differentiation medium with or without PF-573228 (1 μM) for 2 weeks.

FIGS. 2j and 2k show the results of an immunoblot analysis of total FAK (i) and cell attachment to VnP-16 (j) in osteogenic cells transfected with 100 nM control siRNA or 100 nM FAK siRNA (mean±S.D., n=4) (Con, control siRNA-transfected cells; *P<0.01, **P<0.05).

FIGS. 3a and 3b show the three-dimensional μCT images (a) and bone recovery rate (b) in the region of defects 2 weeks after implantation.

FIG. 3c shows the results of Masson's trichrome staining of rat calvarial sections to visualize mineralized bone 2 weeks after implantation.

FIG. 3d shows the images of osteogenic cells and their number of rat calvarial sections in the mineralized bone 2 weeks after implantation. Red and black triangles indicate the wound edges (scale bars, 1.0 mm).

FIG. 3e shows the results with regard to the expression levels of osteogenic markers analyzed by qRT-PCR in rat calvarial sections 2 weeks after implantation. The results are expressed as mean±S.D. (n=4); *P<0.01.

FIGS. 4a to 4d show the results of BMMs cultured on plates precoated with vehicle (DMSO), vitronectin (0.23 μg/cm$^2$), SP (9.1 μg/cm$^2$), or VnP-16 (9.1 μg/cm$^2$) in the presence of M-CSF (30 ng/mL) and RANKL (100 ng/mL).

FIG. 4a shows the images of the cells which, after culturing, were fixed and stained for TRAP (scale bars, 200 μm).

FIG. 4b shows the results with regard to TRAP-positive multinucleated cells containing three or more nuclei counted as osteoclasts.

FIG. 4c shows the results with regard to the sizes of osteoclasts obtained by measuring the diameter of multinucleated TRAP-positive cells on 40× photomicrographs.

FIG. 4d shows the images with regard to the inhibition of F-actin mediated cytoskeletal organization by VnP-16. BMMs were cultured on slides precoated with vehicle (DMSO), SP (9.1 μg/cm$^2$), or VnP-16 (9.1 μg/cm$^2$) in the presence of M-CSF (30 ng/mL) and RANKL (100 ng/mL) for 6 days and then immunostained with DAPI and rhodamine-phalloidin (red) (scale bars, 200 μm).

FIGS. 4e and 4f show the results with regard to the effects of VnP-16 on bone resorptive activity of osteoclasts. BMMs were cultured on Osteo Assay Surface plates precoated with vehicle (DMSO), vitronectin (0.23 μg/cm$^2$), or synthetic peptides (9.1 μg/cm$^2$) in the presence of M-CSF (30 ng/mL) and RANKL (100 ng/mL) for 6 days.

FIG. 4e shows the images of resorption pits photographed after removing cells. Blue arrowheads indicate resorption pits generated by osteoclasts (scale bars, 200 μm).

FIG. 4f shows a graph illustrating the level of bone resorption assessed by measuring the area of resorption pits.

FIG. 4g shows a graph illustrating the effects of VnP-16 at the concentration of 9.1 μg/cm$^2$, which blocks osteoclast differentiation, on cell differentiation and viability of BMMs.

FIG. 4h shows the results of an immunoblot assay with regard to osteoclastogenesis-related genes. BMMs were cultured on plates pretreated with SP (9.1 μg/cm$^2$) or VnP-16 (9.1 μg/cm$^2$) in the presence of M-CSF (30 ng/mL) and RANKL (100 ng/mL) for 1, 2, or 3 days.

FIG. 4i shows the results of an immunoblot assay with regard to MAPKs. BMMs were cultured on plates precoated with SP (9.1 μg/cm$^2$) or VnP-16 (9.1 μg/cm$^2$) in the presence of M-CSF (30 ng/mL) and RANKL (100 ng/mL), serum-starved for 3 hours, and stimulated with M-CSF (30 ng/mL) and RANKL (100 ng/mL) for the indicated times. Whole cell lysates were subjected to western blot with the indicated antibodies.

FIG. 5a shows the results of the immunoblot assays of c-Src, PYK2, and CREB in BMMs. BMMs were cultured on plates precoated with SP (9.1 μg/cm$^2$) or VnP-16 (9.1 μg/cm$^2$) in the presence of M-CSF (30 ng/mL) and RANKL (100 ng/mL) for 1 day, serum-starved for 3 hours, and then stimulated with M-CSF (30 ng/mL) and RANKL (100 ng/mL) for the indicated times.

FIG. 5b shows the results of the immunoblot assays of c-Src, PYK2, and CREB in preosteoclasts. BMMs were cultured on plates precoated with SP (9.1 μg/cm$^2$) or VnP-16 (9.1 μg/cm$^2$) in the presence of M-CSF (30 ng/mL) and RANKL (100 ng/mL) for 3 days, serum-starved for 3 hours, and then stimulated with M-CSF (30 ng/mL) and RANKL (100 ng/mL) for the indicated times.

FIG. 5c shows the results of the immunoblot assays of c-Src, PYK2, and CREB in mature osteoclasts. BMMs were cultured on plates precoated with SP (9.1 μg/cm$^2$) or VnP-16 (9.1 μg/cm$^2$) in the presence of M-CSF (30 ng/mL) and RANKL (100 ng/mL) for 1 day, serum-starved for 3 hours, and then stimulated with M-CSF (30 ng/mL) and RANKL (100 ng/mL) for the indicated times.

FIG. 5d shows the results of the immunoblot assay of active GTP-bound Rac1 in BMMs. The assay conditions were the same as described in FIG. 5a except for the indicated time. The cells were lysed and reacted with PAK1 PBD agarose beads at 4° C. for 1 hour. Active GTP-bound Rac1 proteins were detected by immunoblotting using an anti-Rac1 antibody.

FIG. 5e shows the results of the immunoblot assay of active GTP-bound Rac1 in preosteoclasts. The assay conditions were the same as described in FIG. 5b except for the indicated time. The cells were lysed and reacted with PAK1 PBD agarose beads at 4° C. for 1 hour. Active GTP-bound Rac1 proteins were detected by immunoblotting using an anti-Rac1 antibody.

FIGS. 6a and 6b show the experimental results of BMMs which were cultured on Osteo Assay Surface plates precoated with vehicle (DMSO), vitronectin (0.23 μg/cm$^2$), or SP (9.1 μg/cm$^2$) in the presence of M-CSF (30 ng/mL) and RANKL (100 ng/mL) for 6 days.

FIG. 6a shows the images of resorption pits photographed after removing cells. Blue arrowheads indicate resorption pits generated by osteoclasts (scale bars, 200 μm).

FIG. 6b shows a graph illustrating the level of bone resorption assessed by measuring the area of resorption pits.

FIGS. 6c to 6h show the analysis results of calvarial bone of 5-week-old ICR mice implanted with a collagen sponge (4 mm in diameter), which was treated with vehicle (DMSO), IL-1 (2 μg), synthetic peptide (SP or VnP-16; 125 μg each) or the synthetic peptide simultaneously with IL-1 (2 μg).

FIG. 6c shows the three-dimensional μCT images and TRAP staining of whole calvariae in which black spots indicate eroded surfaces.

FIG. 6d shows the results of calvarial bone volume measured by μCT analysis.

FIG. 6e shows the results of bone mineral content measured by μCT analysis.

FIG. 6f shows the results of histological sections of calvarial bones stained with hematoxylin and eosin (H&E) and histochemically for TRAP.

FIG. 6g shows a graph illustrating osteoclast number confirmed by histomorphometric analysis.

FIG. 6h shows a graph illustrating surface areas of osteoclasts confirmed by histomorphometric analysis.

Figure 6A:
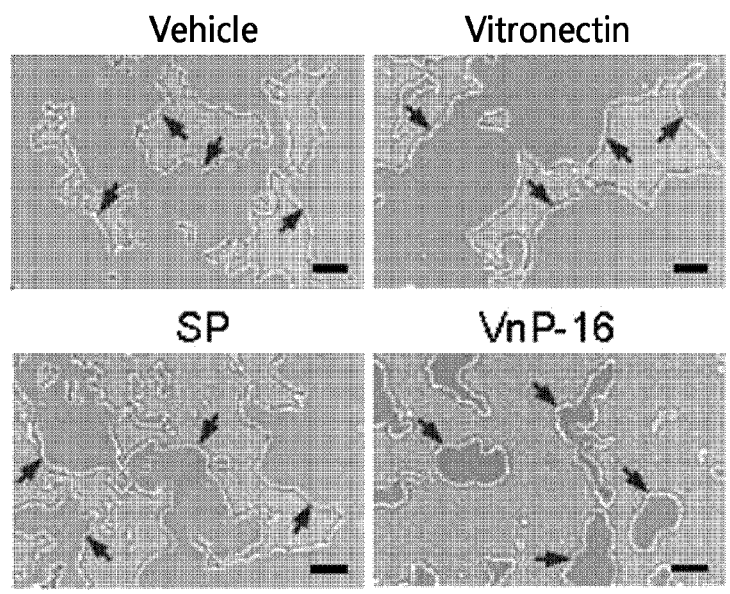
FIGS. 6a to 6h show the results with regard to the effects of VnP-16 on bone resorptive activity in vitro and IL-1-induced bone destruction in vivo.
Figure 6B:
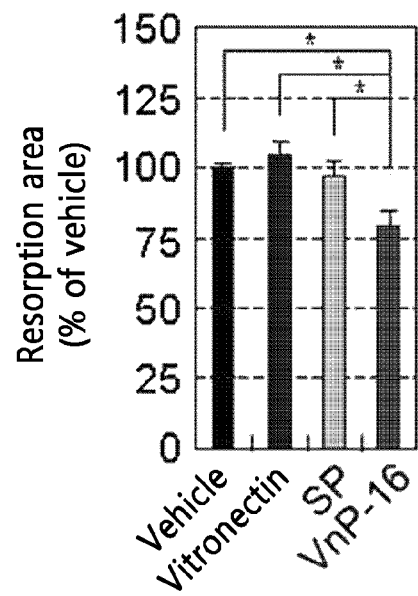
Figure 6C:
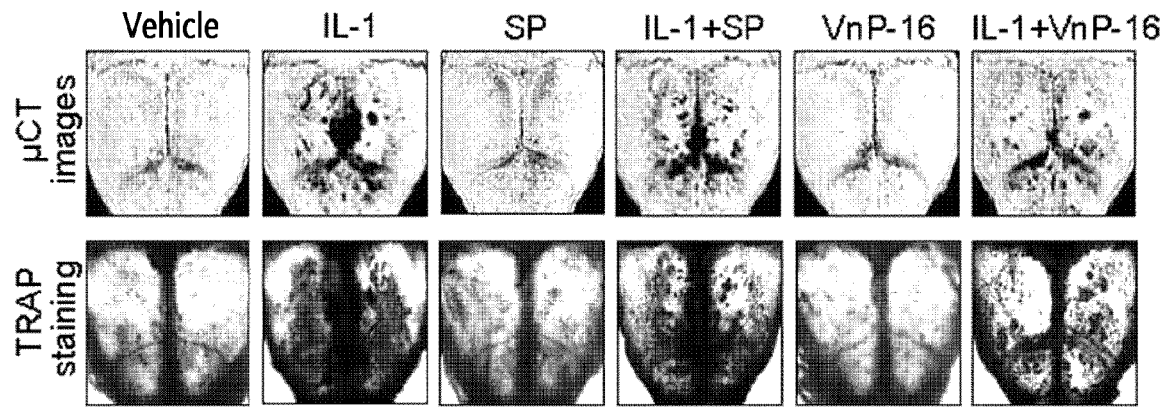
Figure 6D:
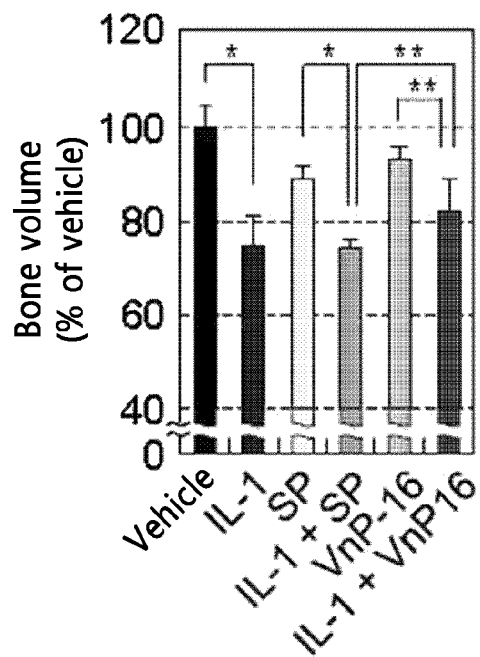
Figure 6E:
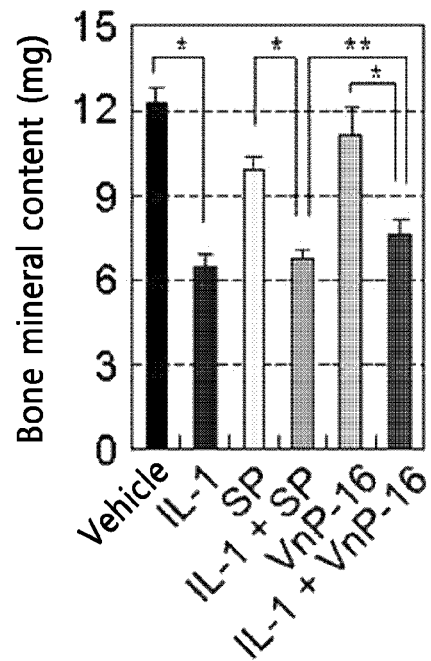

In particular, the results of FIGS. 6b, 6d, and 6e are expressed as mean±S.D. (n=4) (*P<0.01 and **P<0.05).

FIGS. 7a to 7d show the analysis results of purified recombinant human vitronectin (hereinafter, rVn) truncations by SDS-PAGE and circular dichroism (CD).

Figure 7A:
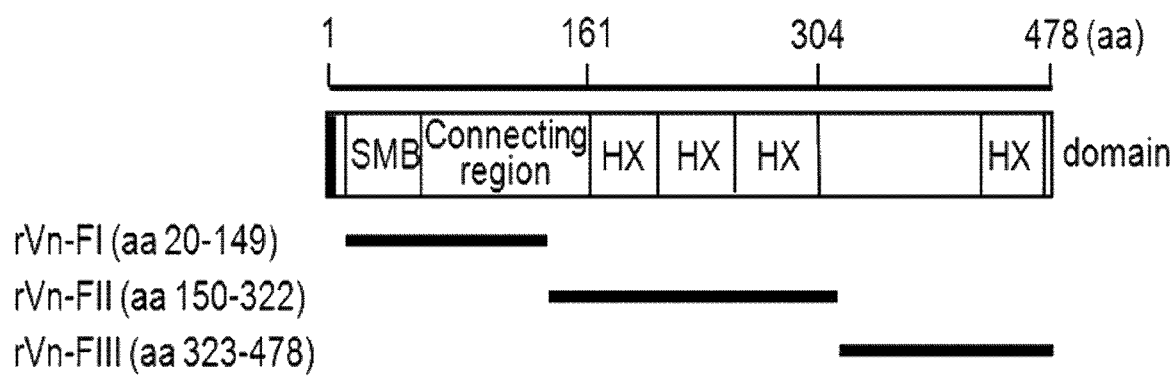

FIG. 7a shows a schematic diagram of rVn truncations. The amino acid (aa) scale is shown on the top and the domain structure of vitronectin is indicated by the open columns. The black column and the closed bars represent the signal peptide and the positions of the recombinant proteins, respectively. Numbers in parentheses correspond to the amino acid positions of the recombinant truncations relative to the full-length protein.

Figure 7B:
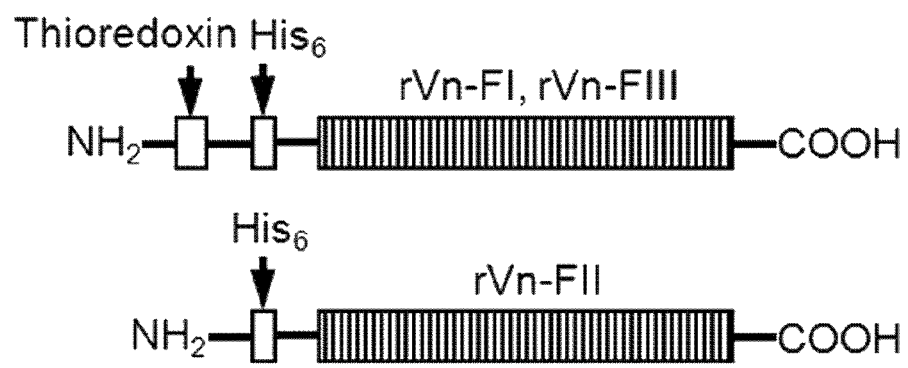
Figure 7B:
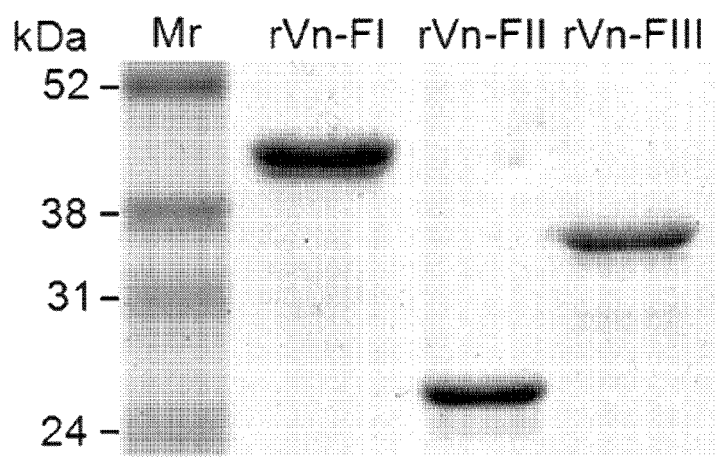

FIG. 7b shows a schematic diagram and SDS-PAGE analysis of the rVn truncations. Each rVn truncation was expressed as a His$_6$-tagged fusion protein. The purified rVn truncations were subjected to SDS-PAGE analysis (10% polyacrylamide gels, reducing conditions) and visualized by Coomassie staining.

Figure 7C:
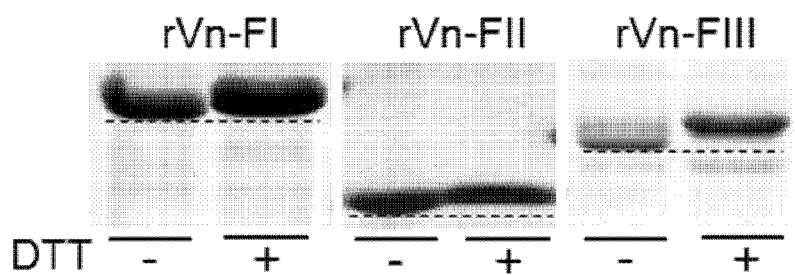

FIG. 7c shows the results with regard to gel mobilities of purified rVn truncations treated with dithiothreitol (DTT) which were compared to those of DTT-untreated rVn truncations by resolving the proteins on 12.5% SDS-PAGE gels.

Figure 7D:
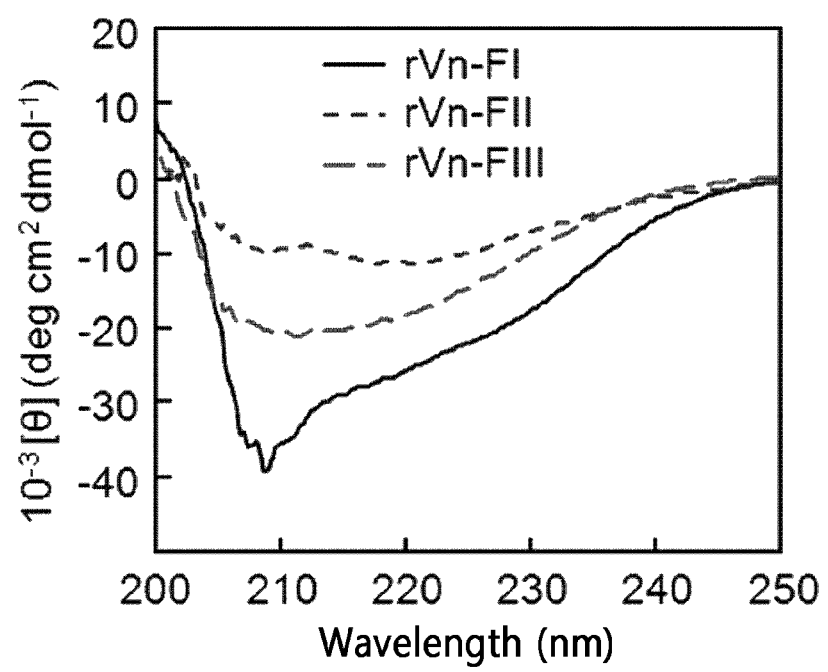

FIG. 7d shows CD analysis of rVn truncations in PBS at pH 3.0 and 23° C.

FIGS. 8a to 8d show the results with regard to cell functions of rVn truncations.

Figure 8A:
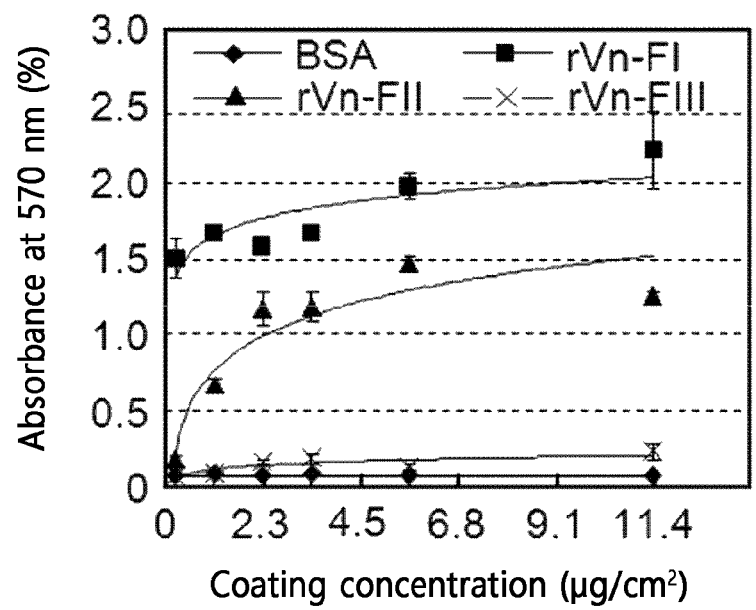

FIG. 8a shows osteogenic cells attached in serum-free medium in a dose-dependent manner.

Figure 8B:
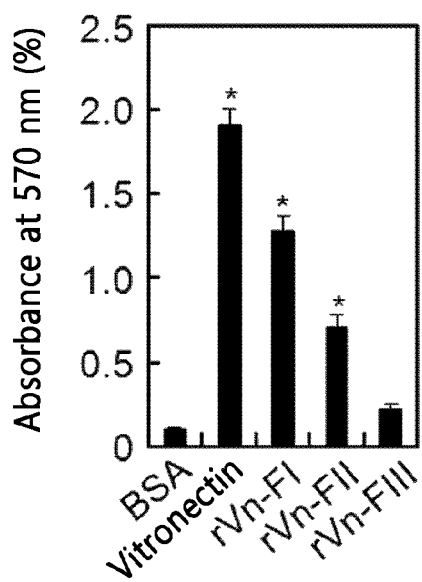

FIG. 8b shows the results with regard to the attachment of osteogenic cells to rVn. The osteogenic cells were seeded on plates precoated with vitronectin (0.23 μg/cm$^2$) and rVn (5.7 μg/cm$^2$) in serum-free medium for 1 hour.

Figure 8C:
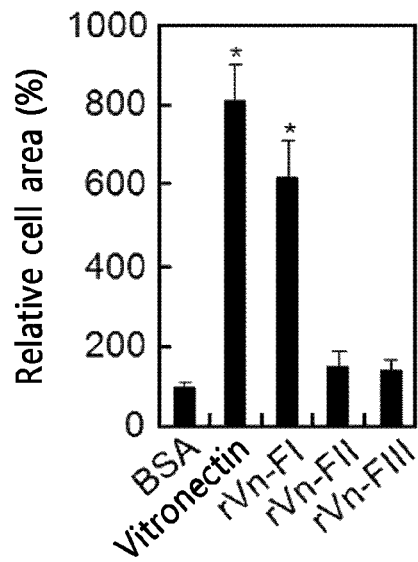

FIG. 8c shows the results with regard to cell spreading induced by vitronectin and rVn truncations. The cells were seeded on plates precoated with vitronectin or rVn in serum-free medium for 3 hours (n=4).

Figure 8D:
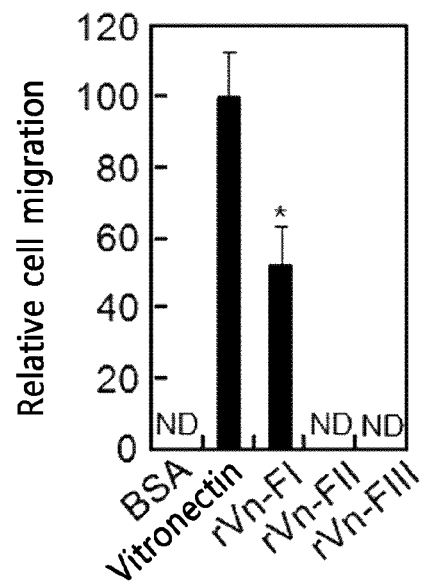

FIG. 8d shows the results with regard to migration of osteogenic cells induced by vitronectin and rVn truncations. Osteogenic cells were seeded into the upper chamber of transwell filters coated with vitronectin or rVn truncations for 24 hours (n=4) (ND: not detected; *P<0.01).

Figure 9:
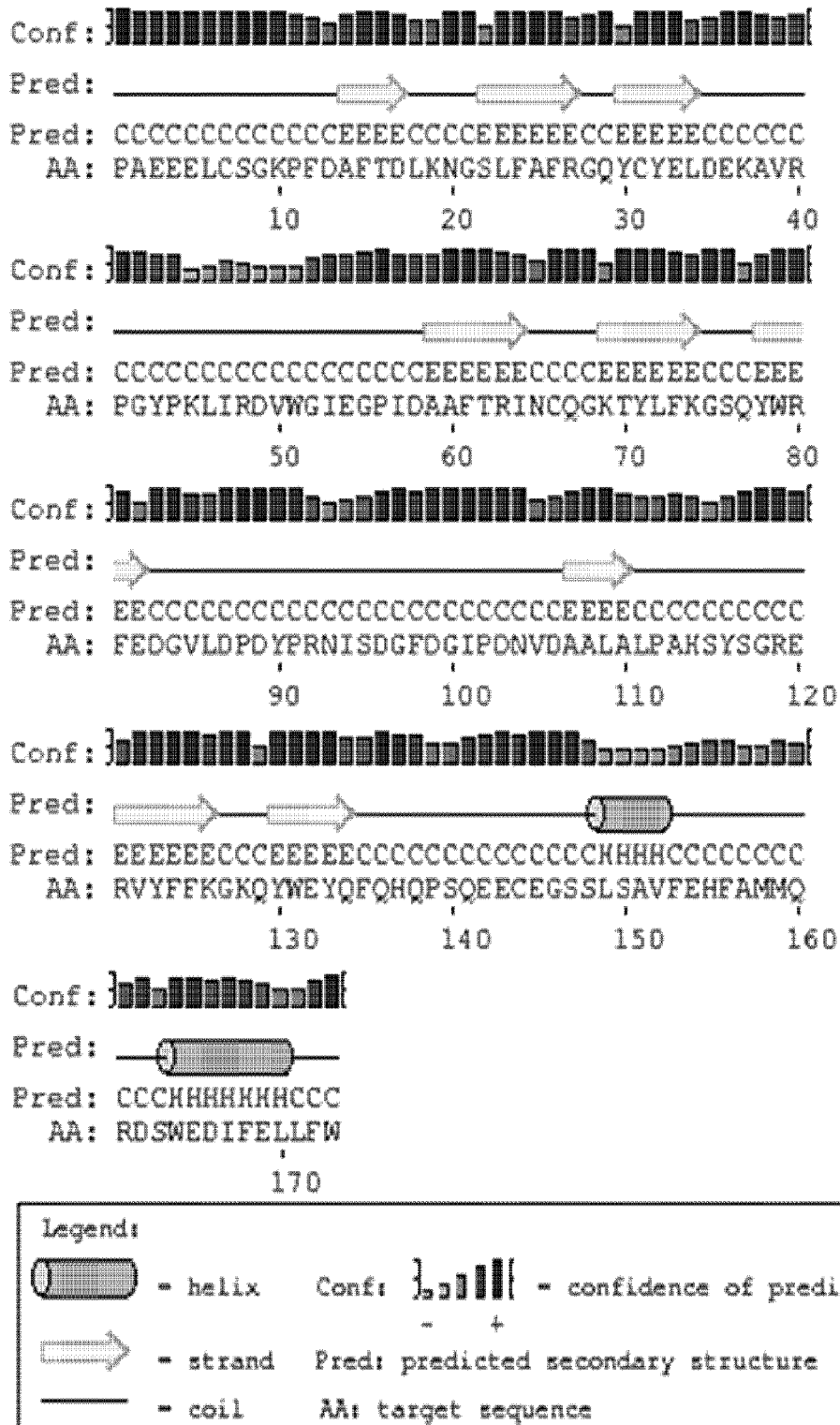

FIG. 9 shows a diagram illustrating a predicted structure of the rVn-FII truncation consisting of 173 residues (amino acids at positions 150 to 322) predicted using the PSIPRED protein structure prediction server. The rVn-FII truncation was predicted to have one α-helix and nine β-strands through structure computation.

Figure 10A:
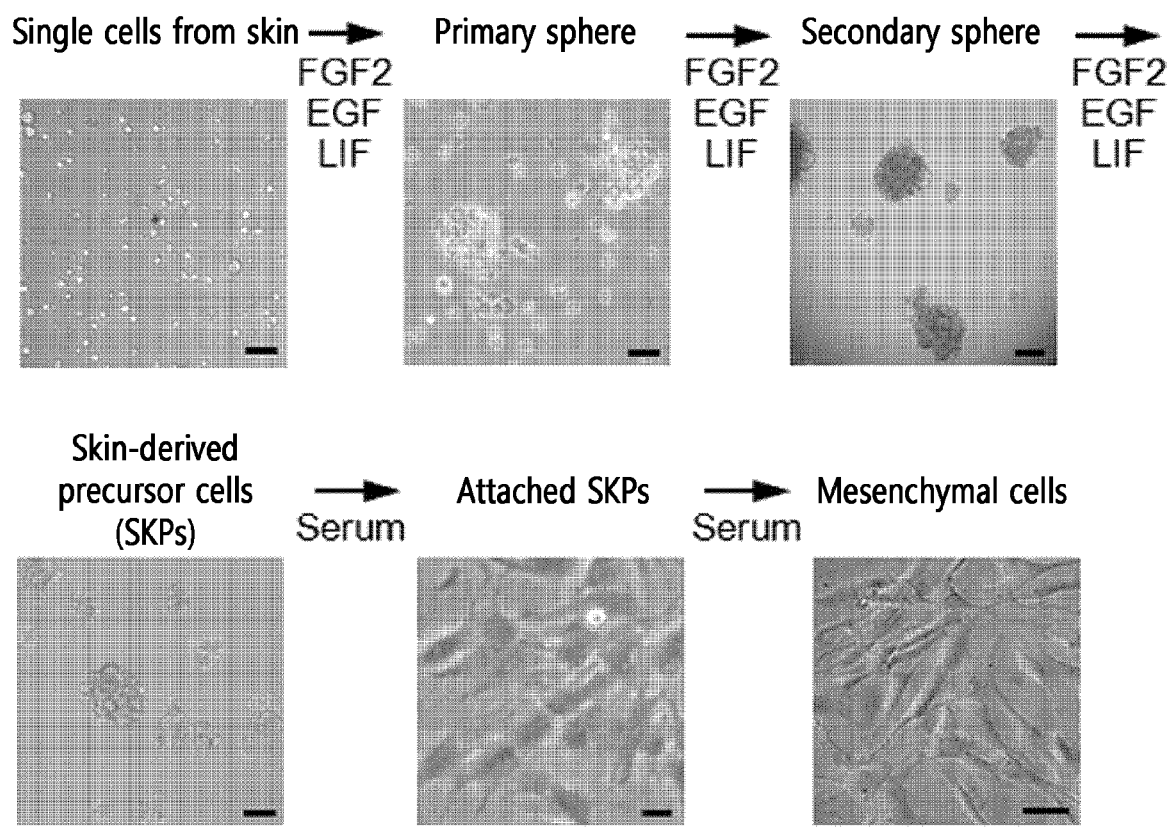
Figure 10B:
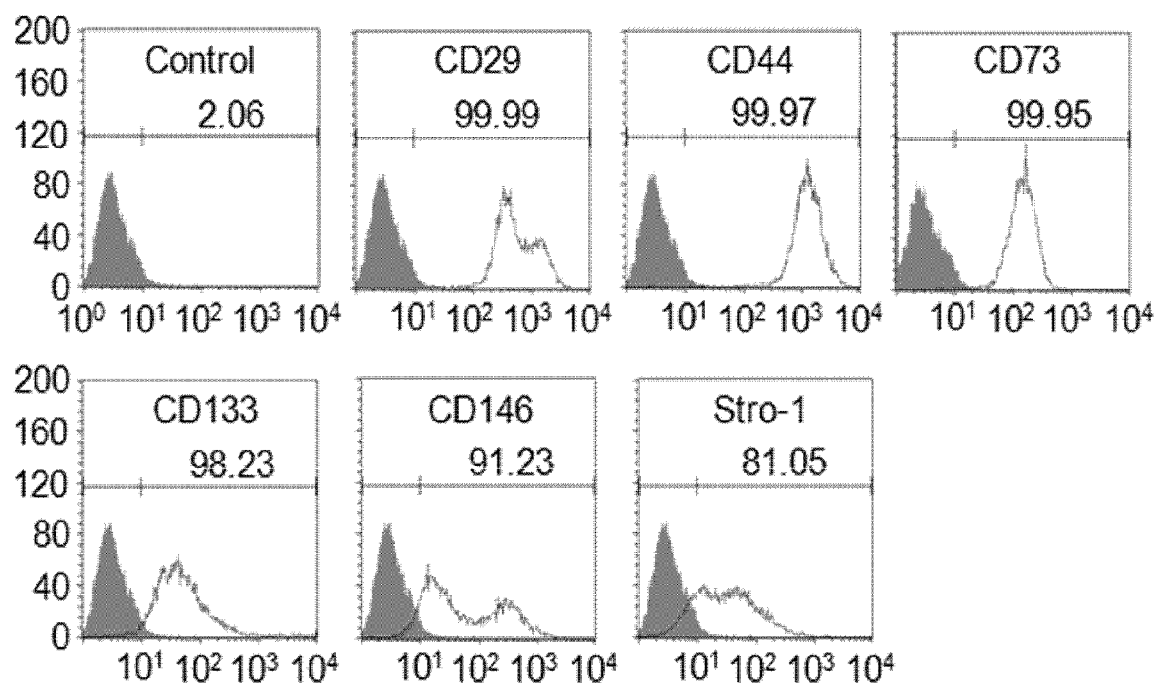
Figure 10C:
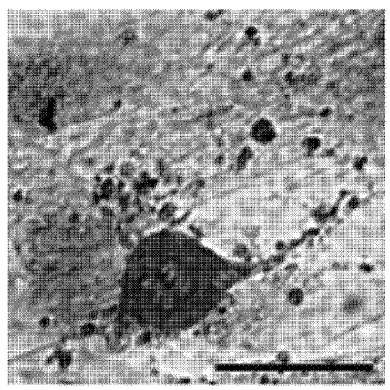
Figure 10D:
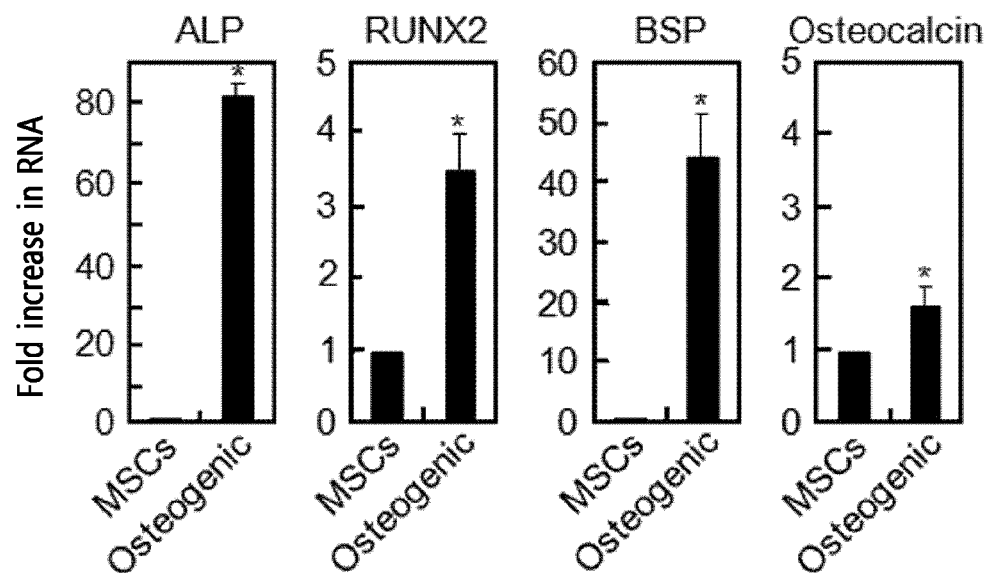
Figure 10E:
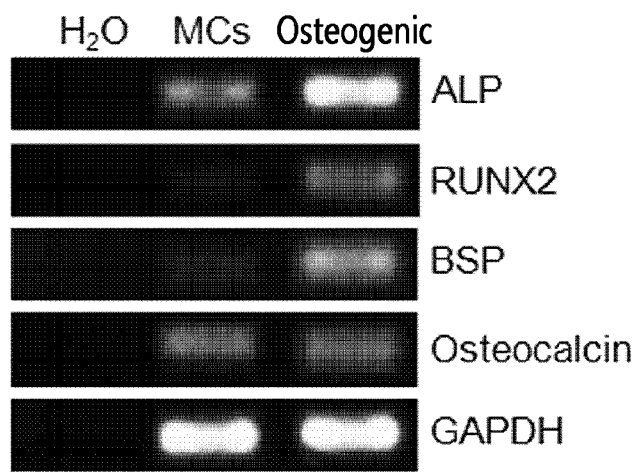

FIGS. 10a and 10e show the results with regard to stepwise isolation of SKPs from human foreskin and directed differentiation from SKPs to mesenchymal precursors to osteogenic cells and their characterization.

FIG. 10a shows a schematic diagram illustrating representative images of the experimental design (upper) and representative images of sphere-forming SKPs (lower) following 7, 14, and 21 days of in vitro expansion. Following the initial purification, SKPs that grew as spheres in suspension were dissociated to single cells and regenerated spheres over the course of one week. The SKPs were exposed to serum and rapidly converted to mesenchymal precursors (scale bar: 50 μm).

FIG. 10b shows the results with regard to a fluorescence-activated cell sorting analysis of the surface marker profiles of SKP-derived mesenchymal precursors.

FIG. 10c shows an image of monolayer cultures of SKP-derived mesenchymal precursors differentiated for two weeks under osteogenic conditions and then stained for mineral deposits using alizarin red S (scale bar: 50 μm).

FIGS. 10d and 10e show the analysis results with regard to expressions of osteogenic markers, including ALP, RUNX2, BSP, and osteocalcin, by qRT-PCR (d) and RT-PCR (e). A reaction without input nucleic acid was run in the first lane as a negative control. The results are expressed as the mean±S.D. (n=4) (*P<0.01).

Figure 11:
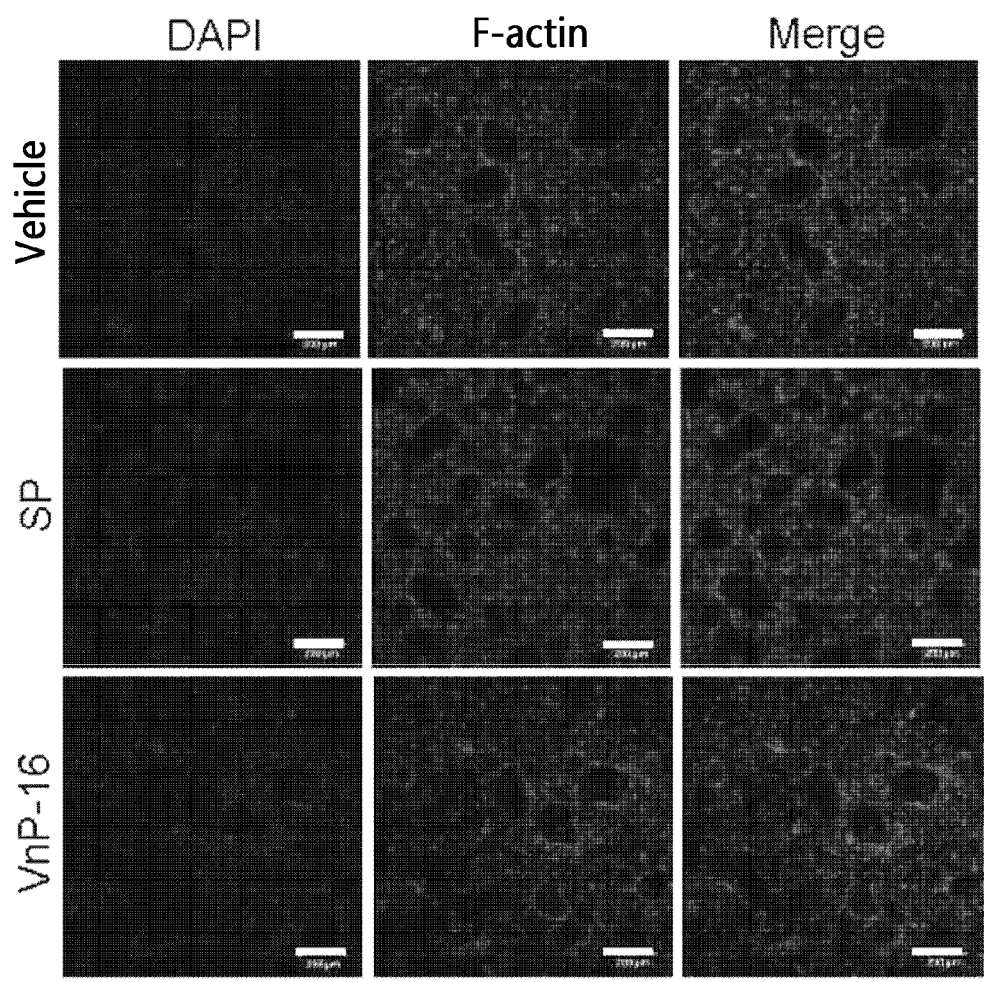

FIG. 11 shows the images with regard to the effects of VnP-16 on F-actin-induced cytoskeletal organization in mature osteoclasts. The osteoclasts were cultured on plates precoated with vehicle (DMSO), SP (9.1 μg/cm$^2$), or VnP-16 (9.1 μg/cm$^2$) in the presence or absence of M-CSF (30 ng/mL) and RANKL (100 ng/mL). The osteoclasts were immunostained with DAPI (blue) and rhodamine-phalloidin (red) (scale bar: 200 μm).

Figure 12:
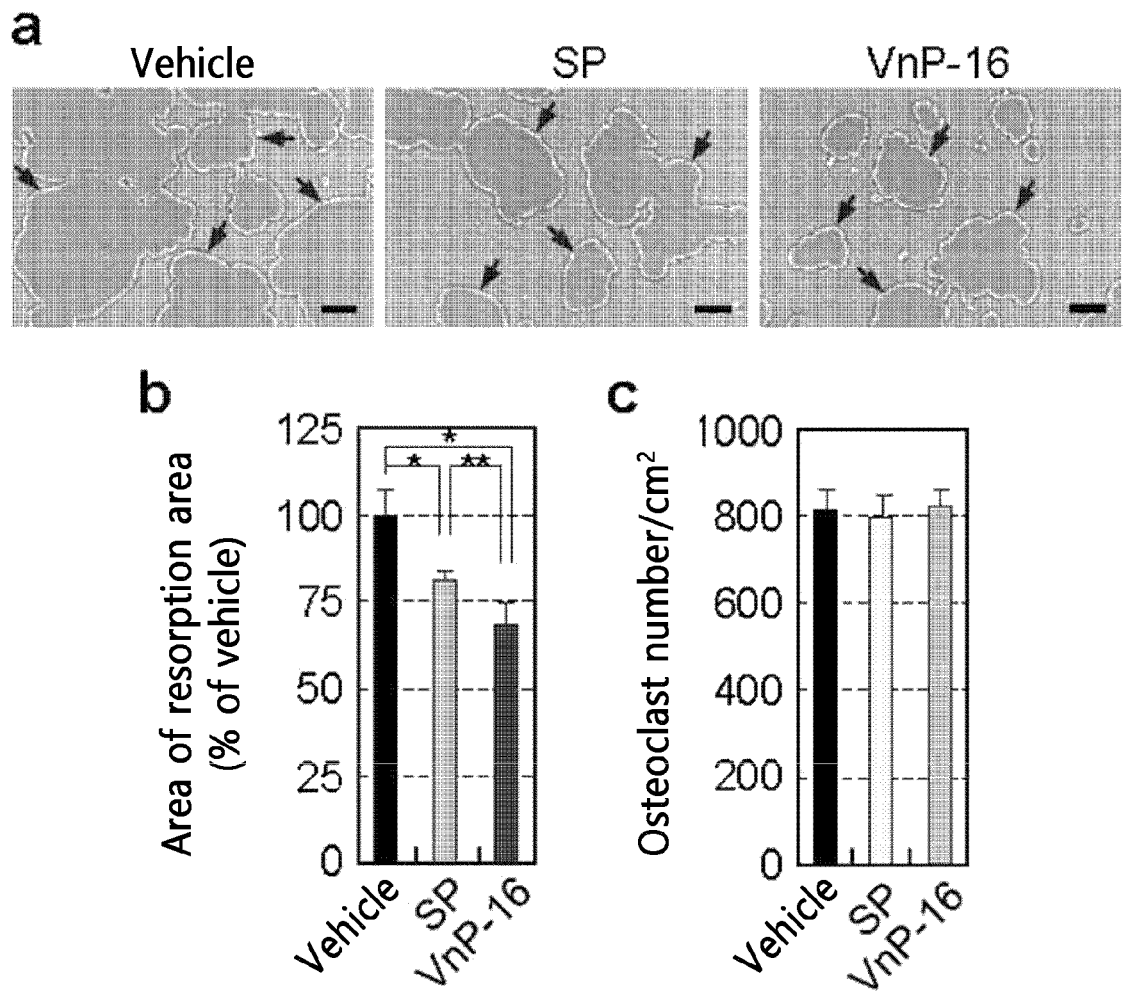

FIGS. 12a to 12c show the results with regard to the effects of VnP-16 on bone resorptive activity and viability of mature osteoclasts. The mature osteoclasts were cultured for 24 hours on Osteo Assay Surface plates precoated with vehicle (DMSO), SP (9.1 μg/cm$^2$), or VnP-16 (9.1 μg/cm$^2$) in the presence of M-CSF (30 ng/mL) and RANKL (100 ng/mL).

FIG. 12a shows images of resorption pits (indicated by blue arrowheads) photographed after removing cells (scale bar: 200 μm).

FIG. 12b shows a graph illustrating the level of bone resorption assessed by measuring the area of resorption pits.

FIG. 12c shows a graph illustrating the number of surviving osteoclasts after TRAP staining. The results of FIGS. 12b and 12c are expressed as mean±S.D. (n=4) (*P<0.01 and **P<0.05.)

BEST MODE

In an aspect to achieve the above object, the present invention provides a peptide for regulating bone formation or bone resorption, which consists of 12 to 173 continuous amino acids comprising the amino acid sequence (RVYFFKGKQYWE) of SEQ ID NO: 17 within the amino acid sequence of SEQ ID NO: 19.

Another aspect of the present invention provides a peptide for regulating bone formation or bone resorption, which contains the amino acid sequence (RVYFFKGKQYWE) of SEQ ID NO: 17. Additionally, the present invention provides a peptide for regulating bone formation or bone resorption, which consists of the amino acid sequence (RVYFFKGKQYWE) of SEQ ID NO: 17.

As used herein, the term "peptide" refers to a compound in a form where α-amino acids of 2 or more and 200 or less are linked by peptide bonds.

The peptide regulating bone formation and resorption of the present invention includes the amino acid sequence of SEQ ID NO: 17 within the amino acid sequence of SEQ ID NO: 19. Specifically, the peptide of the present invention is a peptide consisting of 12 to 173 continuous amino acids, or 12 to 80 continuous amino acids, or 12 to 40 continuous amino acids, or 12 to 14 continuous amino acids, or 12 to 13 continuous amino acids, including the amino acid sequence of SEQ ID NO: 17 within the amino acid sequence of SEQ ID NO: 19, which exhibits the activities of regulating bone formation and bone resorption. Any peptide in which a different amino acid, peptide, etc. is fused to the above amino acid sequences, and which is capable of exhibiting the activities of regulating bone formation and bone resorption, will belong to the scope of the present invention.

In an exemplary embodiment of the present invention, it was confirmed that the peptide for regulating bone formation or bone resorption increases the osteoblast number in the calvarial bone with defects (FIG. 3d), inhibits RANKL-induced osteoclast formation (FIGS. 4a and 4b) and osteoclast differentiation (FIGS. 4h and 4i), inhibits RANKL-induced bone resorption (FIG. 5), decreases the number and area of resorption pits increased by IL-1 (FIGS. 6a and 6b), and decreases the number and area of osteoclasts increased by IL-1 (FIGS. 6c to 6h). This implies that the peptide of the present invention promotes bone formation by regulating bone formation or bone resorption, and thus the peptide can be effectively used for the prevention and treatment of bone diseases.

The peptide of the present invention can be prepared by a known peptide synthesis or by culturing a transformed host cell. When the peptide of the present invention is prepared by culturing a transformed host cell, the peptide may be produced via transformation by introducing a recombinant vector containing a polynucleotide encoding the peptide of the present invention into a host cell followed by culturing the transformant. For the production of the peptide of the present invention, the transformant may be cultured by appropriately selecting any method known in the art.

The amino acid sequence of the present invention can be readily modified by substitution, deletion, and insertion of one or more amino acids, or a combination thereof. Therefore, in the case of a peptide or protein having a high homology to that of SEQ ID NO: 17, for example, peptides or proteins having a high homology of 70% or higher, preferably 80% or higher to that of SEQ ID NO: 17, must be interpreted to be included in the scope of the present invention.

As used herein, the term "homology" indicates sequence similarity to the amino acid sequence of a wild-type protein, and those sequences which have the homology % equal to or higher than those described above are included. The homology may be determined with the naked eye or using a bioinformatic algorithm which enables homology analyses by aligning the sequences for comparison. The homology between the two amino acid sequences may be expressed as a percentage. Useful automated algorithms is available in the GAP, BESTFIT, FASTA, and TFASTA computer software modules of the Wisconsin Genetics Software Package (Genetics Computer Group, Madison, Wis., USA). Automated algorithms arranged in the modules include Needleman & Wunsch and Pearson & Lipman and Smith & Waterman algorithm sequence arrangement. The algorithms and the homology determined for other useful arrangement are automated in software which includes FASTP, BLAST, BLAST2, PSIBLAST, and CLUSTAL W.

The amino acid sequence of SEQ ID NO: 19 of the present invention may be derived from vitronectin, specifically from human vitronectin, and in particular, vitronectin truncations derived from humans (amino acids at positions 150 to 322).

The amino acid sequence of SEQ ID NO: 19 of the present invention may be derived from vitronectin, specifically from human vitronectin, and in particular, vitronectin truncations derived from humans (amino acids at positions 270 to 281).

As used herein, the term "vitronectin" refers to a glycoprotein which is abundant in the serum, extracellular matrices, and bones, and specifically, vitronectin has activities of promoting cell attachment and spreading.

As used herein, the term "osteoblasts", also called "osteogenic cells", refers to cells which secrete bone matrix extracellularly while the cells themselves are encompassed with bone matrices and converted to bone cells. Osteoblasts are cells differentiated from fibrocytes (fibroblasts), and periosteum is present outside a group of osteoblasts. Although osteoblasts are present inside the group of osteoblasts even after completion of osteoblastogenesis, the number of osteoblasts decreases in old bones.

As used herein, the term "osteoclasts" refers to cells which perform the functions of destruction and resorption of bone tissue. Osteoclasts are very large cells having a diameter of 20 μm to 100 μm, and they contain about 2 to 20 nuclei. The osteoclasts are cells differentiated from macrophages, and osteoclastogenesis is cooperatively induced by macrophage-colony stimulating factor (M-CSF), receptor activator of NF-κB ligand (RANKL), and its co-stimulatory factor.

As used herein, the term "osteogenesis" refers to the process of bone formation, and this means a phenomenon of the formation of bone matrix by osteogenic cells and calcification of bone matrix.

As used herein, the term "bone resorption" refers to the process of releasing calcium from bone tissue and generating pores, and the bones become more brittle, and during the process bone matrices and bone minerals are removed simultaneously. This is a phenomenon that occurs during growth or remodeling of bones, but bone resorption can also occur by inflammation or metastasis of cancer into bones.

In the present invention, the activity of promoting bone formation refers to accelerating osteoblast differentiation, and specifically, the osteoblast differentiation may be induced by the interaction of β1 integrin surface receptors present in osteoblasts, and may also be induced by a signaling pathway activated by FAK phosphorylation.

The β1 integrin surface receptor of the present invention refers to a membrane protein receptor which has the role of crosslinking for the interaction of extracellular matrices (ECM). The integrin, upon receipt of a signal from the outside of a cell, triggers a chemical signaling inside the cell to regulate the chemical composition and physical state of the ECM that controls the cell cycle, shape, motility, etc. The phosphorylation of focal adhesion kinase (FAK) is induced by integrin-mediated signaling. Phosphorylated FAK induces cell differentiation through a sub-signaling pathway in the cell, and specifically in the present invention, induces osteoblast differentiation. The bone destruction-inhibiting activity of the present invention means restricting osteoclast differentiation or bone resorption, and specifically, the restriction of osteoclast differentiation or bone resorption may be induced through the inhibition of the JNK-c-Fos-NFATc1 signaling pathway or inhibition of the Src-PYK2 signaling pathway.

The JNK-c-Fos-NFATc1 signaling pathway is triggered by receptor activator of nuclear factor kappa-B ligand (RANKL), which is a kind of type II membrane protein. The RANKL is involved in the production of various cell types, specifically bone cells, and also plays an important role in differentiation and activation of osteoclasts. RNAKL activates c-Jun N-terminal kinases (JNK) to trigger the signal, and the signal is transferred to the nuclear factor of activated T cells, cytoplasmic 1 (NFATc1), through the c-Fos protein. The activated NFATc1 is involved in osteoclast differentiation by controlling the number of osteoclast-specific genes in cooperation with other transcription factors. Additionally, the Src-PYK2 signaling pathway is also triggered by RANKL, and protein tyrosine kinase 2 (PYK2) is phosphorylated through the intracellular signaling pathway by the activated proto-oncogene tyrosine-protein kinase (Src), and the phosphorylated PYK2 is involved in the bone resorbing activity.

Meanwhile, the signaling of the present invention refers to the process of regulating gene expression by recognizing the external environment and transferring the information to the inside of a cell, and specifically, the ligand binds to the receptor of the cell and triggers signaling, and the process is mediated by the signaling molecules.

In an exemplary embodiment of the present invention, attachment assays with regard to VnP-16 (i.e., human vitronectin-derived truncations of the present invention) were performed in various kinds of cells. As a result, it was confirmed that VnP-16 acts in a fibroblast-specific manner (FIG. 1f).

Figure 2A:
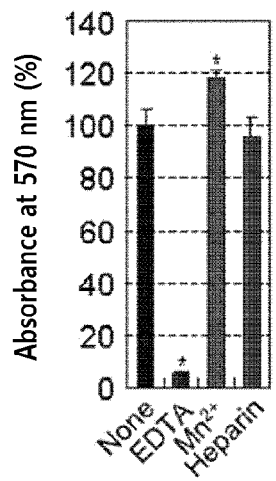
FIGS. 2a to 2k show the results which confirm that VnP-16 induces FAK phosphorylation at Tyr 397 and thereby promotes cell functions and differentiation of osteogenic cells through β1 integrin.
Figure 2B:
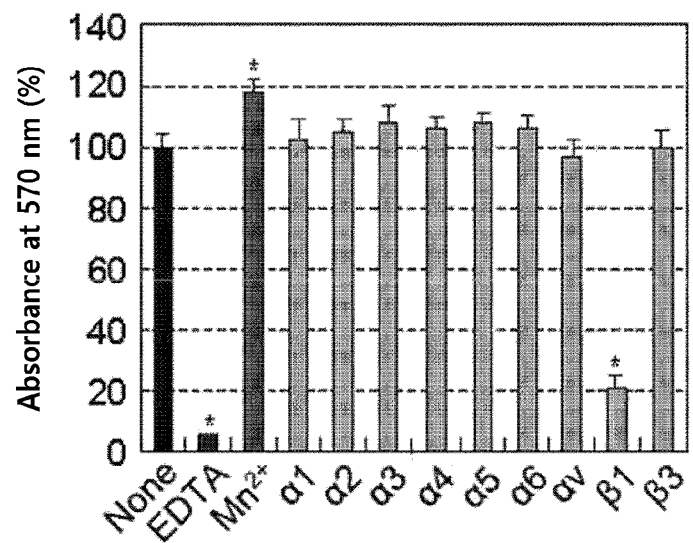
Figure 2C:
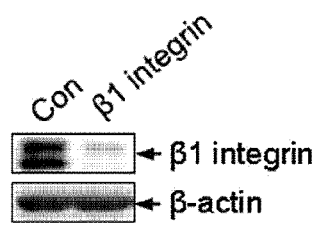
Figure 2D:
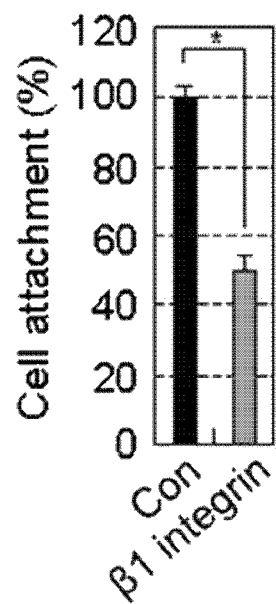

In another exemplary embodiment of the present invention, the cell attachment-mediated function of VnP-16 was examined in cells where the expression of β1 integrin was inhibited by transfection of siRNA. As a result, it was confirmed that β1 integrin functions as a major surface receptor for VnP-16 and thereby mediates cell functions (FIG. 2d).

Figure 2E:
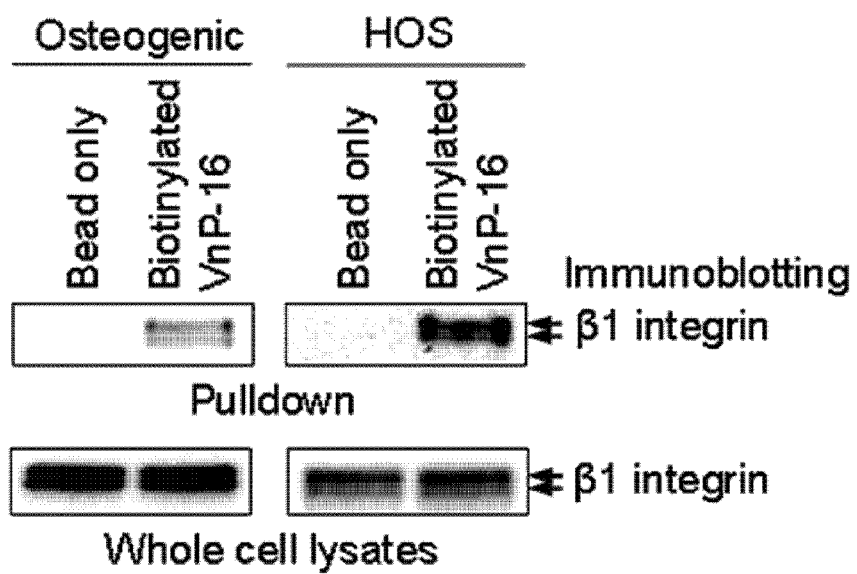
Figure 2F:
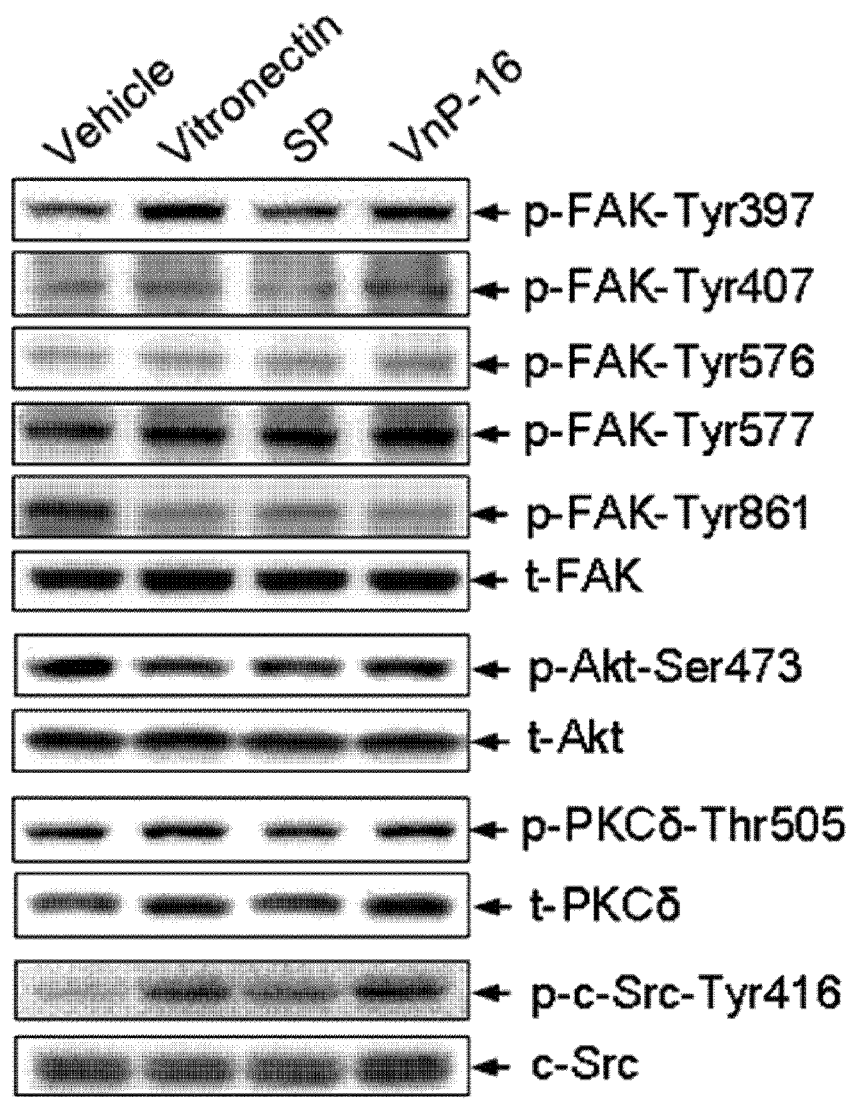
Figure 2G:
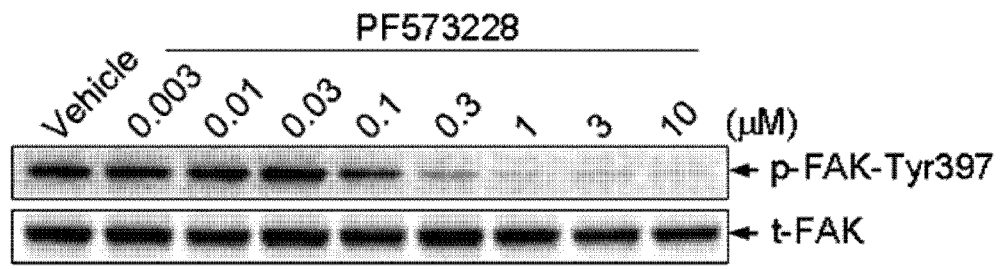
Figure 2H:
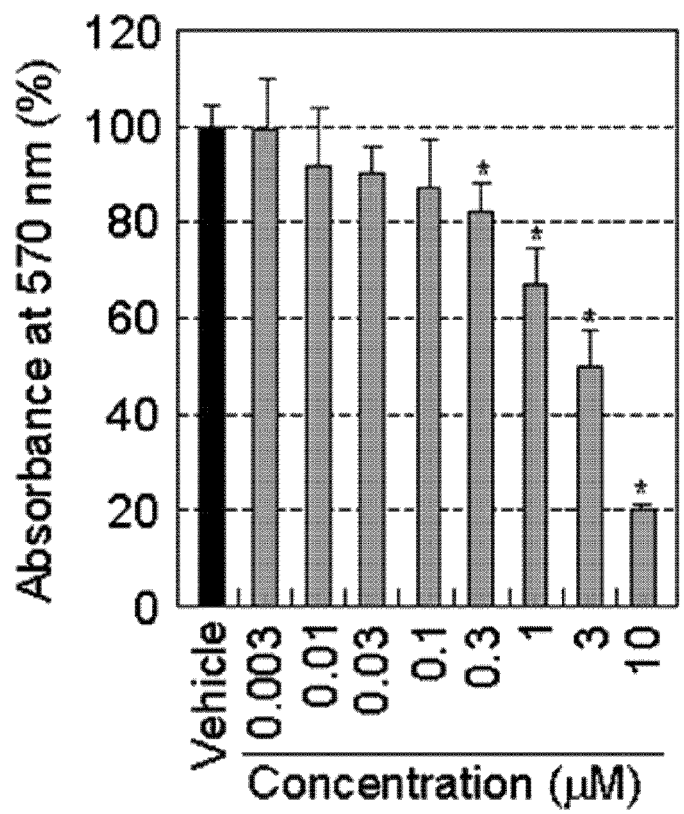
Figure 2I:
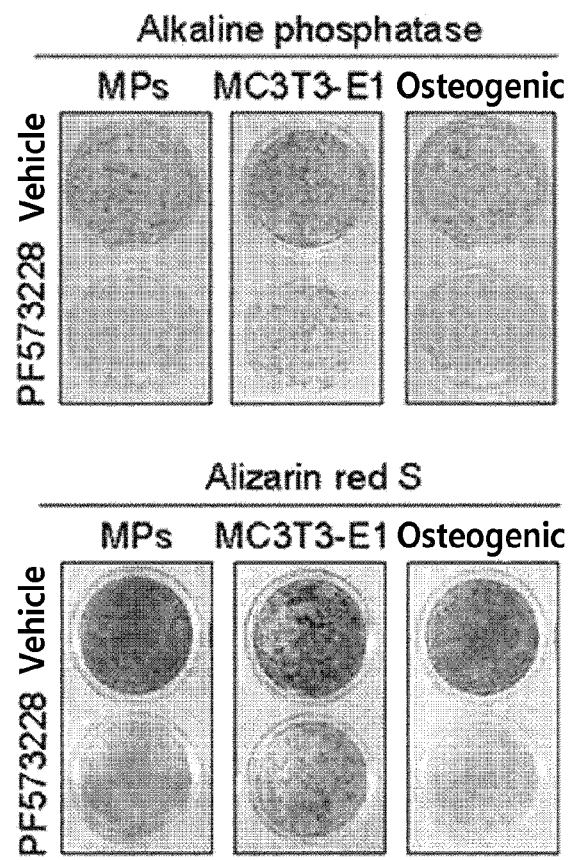

In still another exemplary embodiment of the present invention, the downstream signaling pathway activated in osteoblasts by VnP-16/β1 integrin was examined. As a result, it was confirmed that FAK phosphorylation at Tyr397 is essential for VnP-16/β1 integrin-mediated signaling (FIG. 2f), and also that the FAK phosphorylation at Tyr397 is essential for osteoblast differentiation (FIG. 2i).

In still another exemplary embodiment of the present invention, it was examined whether VnP-16 can promote bone formation in vivo using a rat model with calvarial defects. As a result, it was confirmed that VnP-16 treatment significantly increased the number of osteoblasts compared to that of the control group (FIG. 3d).

Figure 4A:
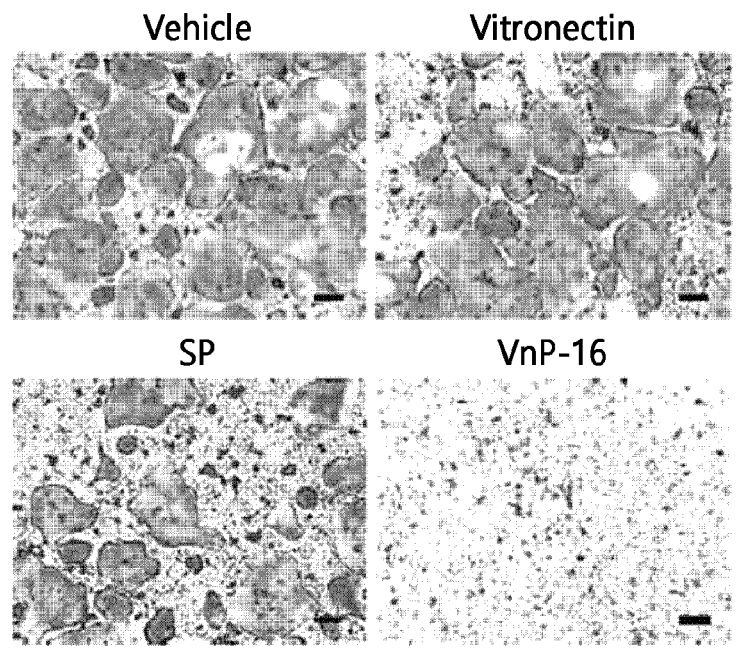
FIGS. 4a to 4i show the effects of VnP-16 on M-CSF and RANKL-induced osteoclast formation and expression levels of osteoclastogenesis-related genes in bone marrow-derived macrophages (BMMs).
Figure 4B:
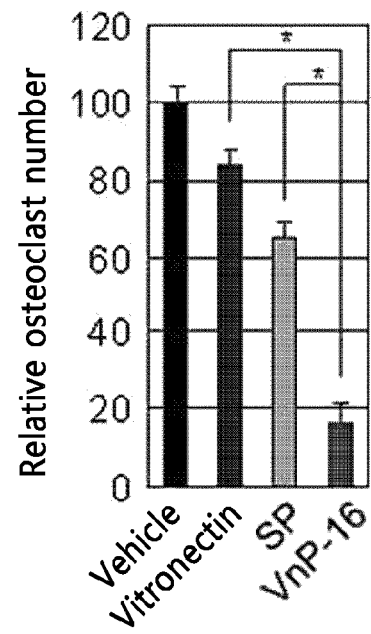
Figure 4C:
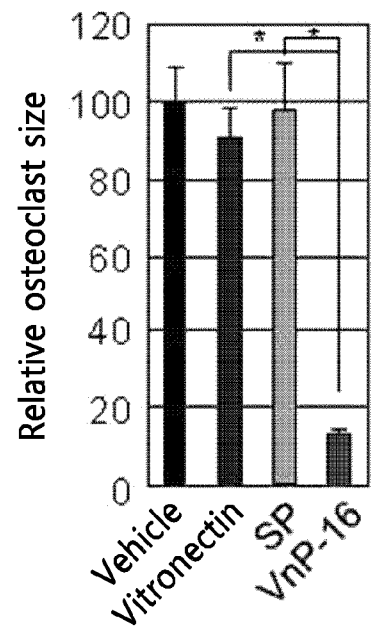
Figure 4D:
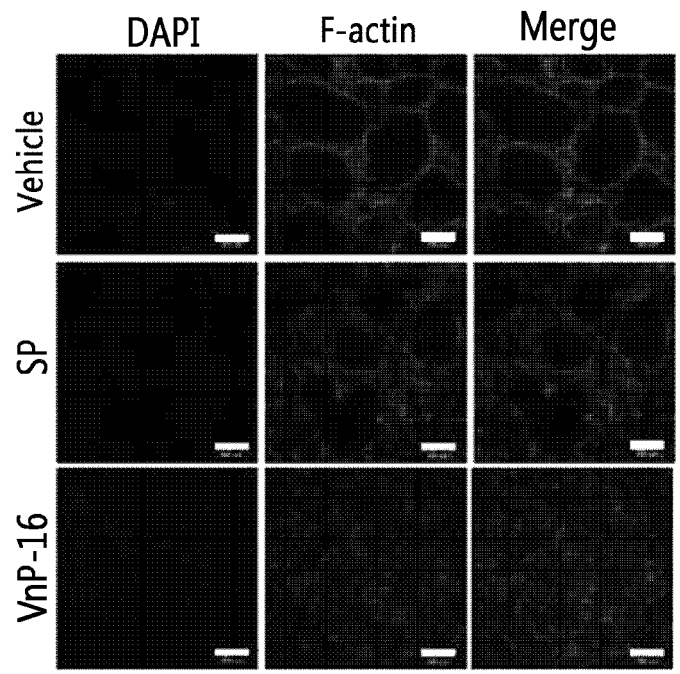
Figure 4E:
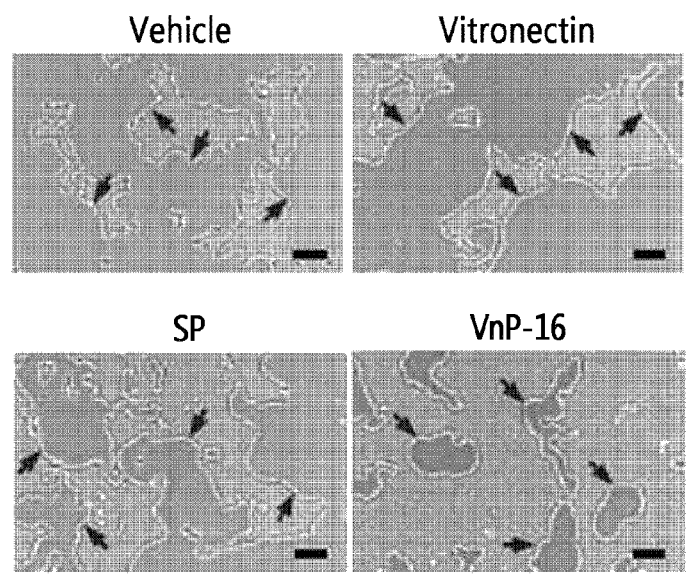
Figure 4F:
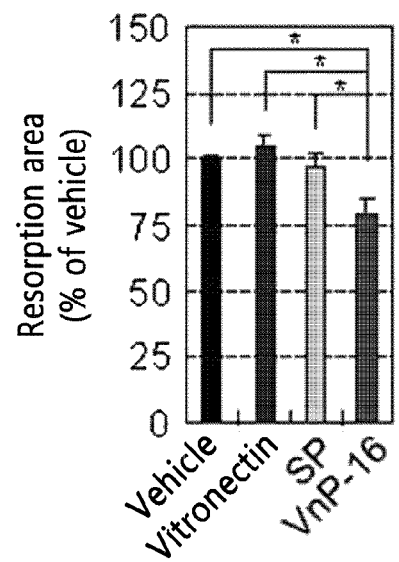
Figure 4G:
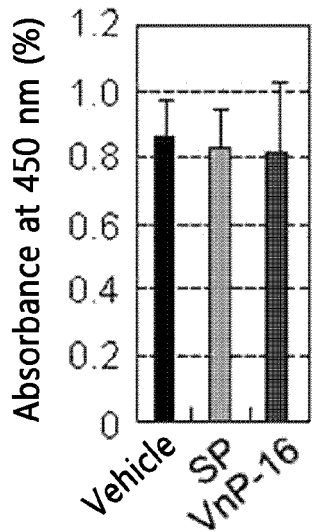
Figure 4H:
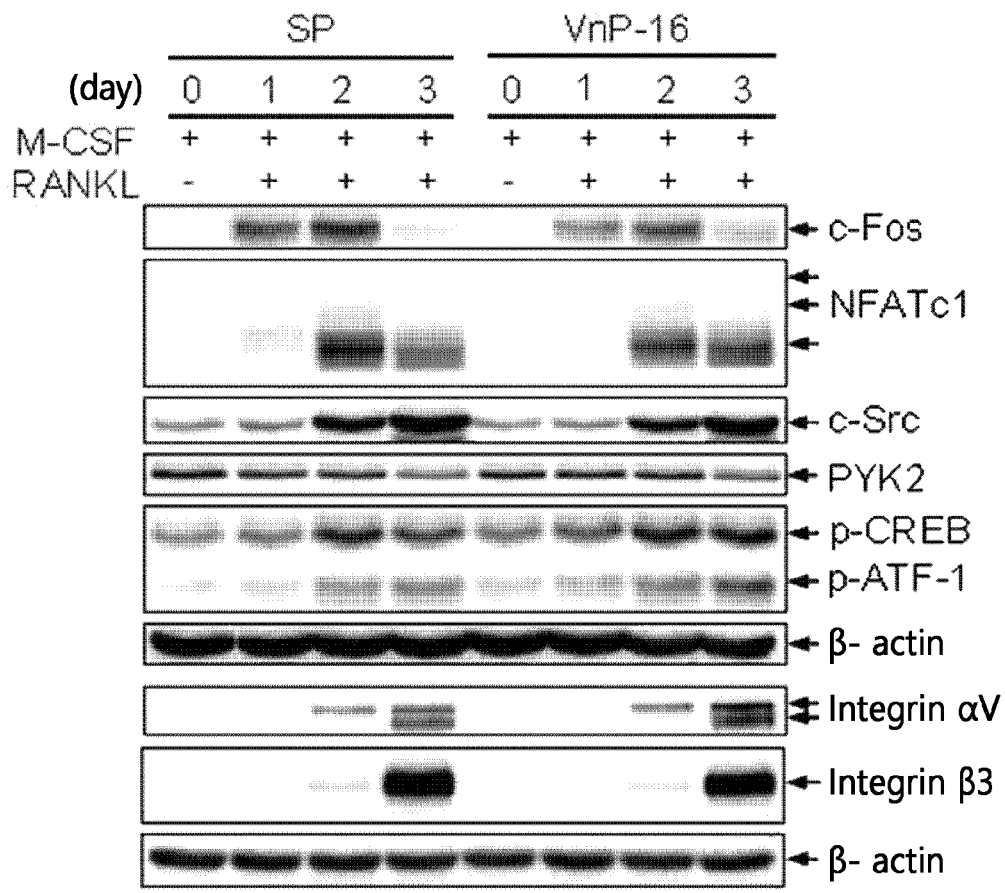
Figure 4I:
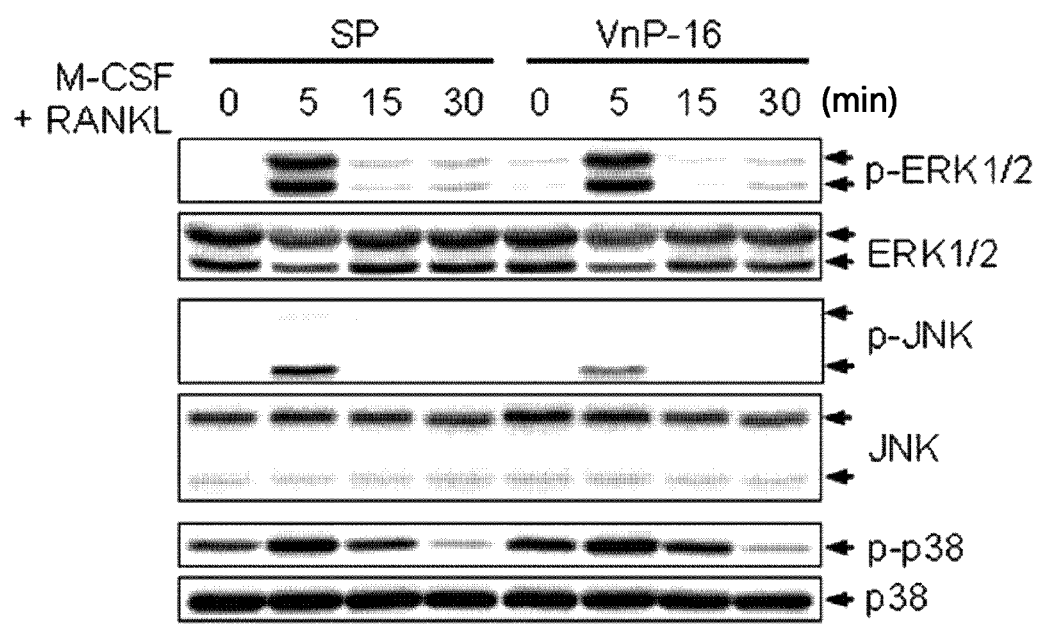

In still another exemplary embodiment of the present invention, it was examined whether VnP-16 can act on the precursor cells of osteoclasts and thereby limit the osteoclast differentiation. As a result, it was confirmed that VnP-16 almost completely inhibits osteoclastogenesis induced by M-CSF and RANKL (FIGS. 4a and 4b) and limits RANKL-induced osteoclast differentiation through the inhibition of JNK-c-Fos-NFATc1 signaling pathway (FIGS. 4h and 4i).

In still another exemplary embodiment of the present invention, it was examined whether αvβ3 integrin signaling is involved in the inhibition of M-CSF- and RANKL-induced resorptive function by VnP-16. As a result, it was confirmed that VnP-16 inhibits RANKL-induced bone resorption through the prevention of Src-PYK2 signaling (FIG. 5).

In still another exemplary embodiment of the present invention, the effect of VnP-16 on bone resorptive function was examined. As a result, it was confirmed that VnP-16 reduces the number of resorption pits and resorption area increased by IL-1 (FIGS. 6a and 6b), and also that VnP-16 reduces the number of osteoclasts and resorption area increased by IL-1 (FIGS. 6c to 6h).

In still another exemplary embodiment of the present invention, the secondary structure of VnP-16 was predicted by CD spectroscopy. As a result, it was confirmed that VnP-16 has the characteristic of a protein rich in β-structure (FIG. 7d).

In still another exemplary embodiment of the present invention, the cell attachment activity for each of the vitronectin-derived truncations was examined. As a result, it was confirmed that rVn-FI and rVn-FII are the most biologically active proteins among the three recombinant truncations (FIG. 8).

In still another exemplary embodiment of the present invention, cell differentiation was performed to examine whether the directed differentiation from skin-derived precursors (SKPs) into osteogenic cells via mesenchymal cells is possible, and the expression levels of osteogenic cell-specific markers were examined. As a result, it was confirmed that SKP-derived mesenchymal cells can differentiate into osteogenic lineage (FIG. 10).

Still another aspect of the present invention provides a polynucleotide encoding the peptide of the present invention and a recombinant vector containing the polynucleotide.

The polynucleotide of the present invention, which is a polymer of nucleotides where nucleotide monomers are linked in a long chain by a covalent bond, refers to a polynucleotide that encodes a peptide according to the present invention as a DNA or RNA strand of a certain length or more.

Additionally, with regard to the polynucleotide of the present invention, various variations or modifications can be made to the coding region within a range that does not change the amino acid sequence of the peptide expressed from the coding region, considering the preferred codon in an organism where the peptide is to be expressed. That is, with regard to the polynucleotide of the present invention, at least one nucleotide may be modified by substitution, deletion, insertion, or a combination thereof, and these are also included in the scope of the present invention.

The recombinant vector of the present invention is a means for introducing the peptide of the present invention into a cell to be expressed in the cell, and known vectors such as plasmid, cosmid, bacteriophage vectors, etc. may be used. The recombinant vector can easily be prepared by a skilled person in the art according to a known method in the art utilizing DNA recombination technology.

Still another aspect of the present invention provides a pharmaceutical composition for preventing or treating bone disease, containing a peptide of the present invention, a polynucleotide encoding the peptide, or a recombinant vector containing the polynucleotide, as an active ingredient.

Still another aspect of the present invention provides a method for preventing or treating bone disease, which includes administering the pharmaceutical composition of the present invention to a subject having bone disease or at risk of developing bone disease.

As used herein, the term "prevention" refers to all of the actions that can inhibit or delay the development of bone disease by the administration of the pharmaceutical composition of the present invention, and the term "treatment" refers to all of the actions that can improve or advantageously change the symptoms due to bone disease by the administration of the pharmaceutical composition of the present invention.

As used herein, the term "subject" refers to all of the animals including humans having bone disease or at risk of developing bone disease. The bone disease may be at least one selected from the group consisting of osteoporosis, Paget's disease, fracture, osteogenesis imperfecta, periodontal disease, and osteoarthritis, but the bone disease is not limited thereto.

The pharmaceutical composition of the present invention may be administered via any of the common routes as long as the composition can arrive at a target tissue (areas with bone defects, etc.) or cell. For example, the pharmaceutical composition of the present invention may be directly/indirectly administered intraperitoneally, intravenously, intramuscularly, subcutaneously, intradermally, orally, intrapulmonarily, intrarectally, and interstitially. For this purpose, the pharmaceutical composition may be administered using a certain apparatus capable of transporting the active ingredient into a target cell.

The pharmaceutical composition of the present invention may include pharmaceutically acceptable carriers. The pharmaceutical composition of the present invention including pharmaceutically acceptable carriers may be various types of oral or parenteral formulations. For the preparation of formulations, the conventional fillers, extenders, binders, humectants, disintegrants, and diluents such as surfactants or excipients may be used. For solid formulations for oral administration, tablets, pills, powders, granules, capsules, etc. may be included. The solid formulations may be prepared by mixing at least one excipient (e.g., starch, calcium carbonate, sucrose or lactose, gelatin, etc.) with at least one compound. Examples of liquid formulations for oral administration may include suspensions, liquid medicine for internal use, emulsions, syrups, etc. and may include various excipients (e.g., humectants, sweeteners, fragrances, preservatives, etc.) in addition to simple diluents such as water and liquid paraffin. Examples of parenteral formulations may include sterile aqueous solutions, non-aqueous solvents, suspensions, emulsions, lyophilized preparations, and suppositories. Examples of non-aqueous solvents or suspending agents may include propylene glycol, polyethylene glycol, vegetable oils such as olive oil, an injectable ester such as ethyl oleate, etc. Examples of substrates to be used for suppositories may include witepsol, microgol, tween 61, cacao butter, laurinum, glycerogelatin, etc. The pharmaceutical composition of the present invention may be prepared in any one formulation type selected from the group consisting of tablets, pills, powders, granules, capsules, suspensions, liquid medicine for internal use, emulsions, syrups, sterile aqueous solutions, non-aqueous solvents, lyophilized formulations, and suppositories.

The pharmaceutical composition of the present invention may be administered in a therapeutically effective or pharmaceutically effective amount. As used herein, the term "therapeutically effective or pharmaceutically effective amount" refers to an amount sufficient for treating a disease with a reasonable benefit/risk ratio applicable to medical treatment, and the level of effective dose may be determined based on factors including type of a subject, severity of disease, age, sex, sensitivity to drug of a subject, duration of administration, routes of administration and drug excretion rate, duration of treatment, drugs used simultaneously, and other factors well known in the medical field.

The pharmaceutical composition of the present invention may be administered alone or in combination with surgery, hormone treatment, drug treatment, and methods using biological response modifiers.

DETAILED DESCRIPTION OF THE INVENTION

Hereinafter, the present invention will be described in more detail with reference to the following Examples. However, these Examples are for illustrative purposes only and the invention is not intended to be limited by these Examples.

Example 1. Use of Peptides and Reagents

All of the peptides of the present invention were synthesized on a Pioneer peptide synthesizer (Applied Biosystems) using the 9-fluorenylmethoxycarbonyl(Fmoc)-based solid-phase method with a C-terminal amide. The peptides were purified and characterized by Peptron (Daejeon, Korea). All of the peptides used in the study had a purity greater than 95% as determined using high performance liquid chromatography. Human vitronectin was purchased from Millipore. The peptides and proteins used are summarized in Table 1 below.

TABLE 1

Peptides and proteins used in the present invention

| Peptide | Sequence |
| --- | --- |
| VnP-16 | RVYFFKGKQYWE (SEQ ID NO: 17) |
| rVn-FI | DQESCKGRCT EGFNVDKKCQ CDELCSYYQS CCTDYTAECK PQVTRGDVFT MPEDEYTVYD DGEEKNNATV HEQVGGPSLT SDLQAQSKGN PEQTPVLKPE EEAPAPEVGA SKPEGIDSRP ETLHPGRPQP (SEQ ID NO: 18) |
| rVn-FII | PAEEELCSGK PFDAFTDLKN GSLFAFRGQY CYELDEKAVR PGYPKLIRDV WGIEGPIDAA FTRINCQGKT YLFKGSQYWR FEDGVLDPDY PRNISDGFDG IPDNVDAALA LPAHSYSGRE RVYFFKGKQY WEYQFQHQPS QEECEGSSLS AVFEHFAMMQ RDSWEDIFEL LFW (SEQ ID NO: 19) |
| rVn-FIII | GRTSAGT RQPQFISRDW HGVPGQVDAA MAGRIYISGM APRPSLAKKQ RFRHRNRKGY RSQRGHSRGR NQNSRRPSRA TWLSLFSSEE SNLGANNYDD YRMDWLVPAT CEPIQSVFFF SGDKYYRVNL RTRRVDTVDP PYPRSIAQYW LGCPAPGHL (SEQ ID NO: 20) |
| VnP-15 | AHSYSGRERVYF (SEQ ID NO: 21) |
| VnP-17 | QYWEYQFQHQPS (SEQ ID NO: 22) |
| Scrambled Peptide (SP) | FVWRQFYKYEKG (SEQ ID NO: 23) |

Example 2. Determination of Secondary Structure of rVn-FII and VnP-16

The secondary structures of the rVn-FII truncation and VnP-16 peptide were analyzed using the Psi-blast based secondary structure prediction (PSIPRED) method and by an ab initio technique for computational structure prediction.

Example 3. Preparation of Cells and Directed Differentiation from Osteogenic Cells to Skin-Derived Precursors (SKPs)

The PC12 cell line from implantable rat pheochromocytoma was purchased from the American Type Culture Collection (ATCC) and cultured in RPMI 1640 medium containing 10% FBS. The mouse embryo fibroblast cell line NIH/3T3, a normal African green monkey kidney fibroblast cell line (CV-1), and a murine osteoblastic cell line (MC3T3-E1) were purchased from the ATCC and cultured in DMEM containing 10% FBS. For osteogenic differentiation, MC3T3-E1 cells were cultured in α-MEM supplemented with 0.1 μM dexamethasone, 173 μM ascorbic acid, 10 mM β-glycerol phosphate, and 10% FBS for two weeks. The medium was changed every two days and cultures were maintained for two weeks without subculturing Primary normal human epidermal keratinocytes (NHEKs), normal human oral keratinocytes (NHOKs), normal human skin fibroblasts (NHDFs), and normal human oral fibroblasts (NHOFs) were prepared and maintained as described in references (Yeo, I. S. et al. *Biomacromolecules*, 9, 1106 to 1116 (2008) and Min, B. M. et al. *Biomaterials*, 25, 1289 to 1297 (2004)).

Multipotent SKPs were isolated from the human foreskins of patients (1 to 3 years old) who had had surgery. Briefly, skin samples composed of epidermis and dermis were dissected, cut into small pieces, and digested in 0.1% trypsin-EDTA in calcium- and magnesium-free Hanks' balanced salt solution for 60 minutes at 37° C. Partially digested skin pieces were mechanically dissociated and filtered through a 40 μm cell strainer (BD Biosciences). The filtered cells were washed, resuspended, and plated on T25 culture flasks. The cells were grown in DMEM/F12 (vol/vol, 1:1) medium supplemented with 1×B-27 supplement (Invitrogen), 20 ng/mL fibroblast growth factor 2 (FGF2), 20 ng/mL epidermal growth factor (EGF; PeproTech), and 10 ng/mL leukemia inhibitory factor (LIF) for one week, and growth factors were added to the medium every 2 days without changing the medium.

For the serial sphere formation assays, subculturing was performed once a week for three weeks after the dissociation of the spheres with accutase (Innovative Cell Technologies).

Then, SKPs were differentiated into mesenchymal cells. The tertiary spheres were dissociated to single cells with accutase and cultured in α-MEM supplemented with 10% FBS. Attached cells were subcultured up to reaching 80% confluence, and third passage cells were used as SKP-derived mesenchymal cells. For osteogenic differentiation, SKP-derived mesenchymal cells were cultured in α-MEM supplemented with 10 μM dexamethasone, 200 μM ascorbic acid, 10 mM β-glycerol phosphate, and 10% FBS for two weeks. The medium was changed every 2 days and cultures were maintained for two weeks without subculturing All procedures for obtaining human tissue specimens were performed according to the Guidelines of the Institutional Review Board on Human Subjects Research and the Ethics Committee at Seoul National University Dental Hospital, Seoul, Korea.

Example 4. Preparation of Bone Marrow-Derived Macrophage (BMMs)

To obtain bone marrow-derived macrophages (BMMs), bone marrow cells were collected by flushing the tibias and femurs of 6-week-old male C57BL/6 mice (Orient) and then cultured in α-MEM complete media containing 10% FBS (Invitrogen), 100 U/mL penicillin, and 100 μg/mL streptomycin on 100 mm culture dishes in the presence of M-CSF (10 ng/mL) after removing the red blood cells with ACK buffer (0.01 mM EDTA, 0.011 M $KHCO_3$, and 0.155 M $NH_4Cl$, pH 7.3). Cells not attached to the culture plates were further cultured with 30 ng/mL mouse M-CSF for 3 days, and the attached cells were used as BMMs.

Example 5. Osteoclast Differentiation Assay

To generate osteoclasts from BMM cultures, BMMs ($2\times10^5$ cells/well) were cultured on 48-well culture plates coated with vehicle (DMSO), vitronectin (0.23 µg/cm$^2$), and VnP-16 peptide (9.1 µg/cm$^2$) in the presence of M-CSF (30 ng/mL) and mouse water-soluble RANKL (100 ng/mL) for 6 days. The complete medium was replaced at day 3 and day 5. After the cultures, the cells were fixed and stained with TRAP, a marker enzyme for osteoclasts.

Example 6. Cell Attachment and Spreading Assays

Cell attachment assays were performed on 48-well culture plates coated with human plasma vitronectin (0.23 µg/cm$^2$) or rVn-FII (5.7 µg/cm$^2$) at 4° C. for 18 hours. VnP-16 peptide (9.1 µg/cm$^2$) was adsorbed onto plates by drying at room temperature for 18 hours. The concentrations of the recombinant protein and synthetic peptides were determined from a dose-response curve, and the lowest concentration necessary to achieve maximum attachment to human osteogenic cells was used. The concentration of human plasma vitronectin was determined according to the manufacturer's instructions. The substrate-coated plates were blocked with 1% heat-inactivated BSA in PBS at 37° C. for 1 hour and then washed with PBS. Osteogenic cells were detached with trypsin/EDTA and resuspended in serum-free culture medium. Cells ($5\times10^4$ cells/250 µL) were added to each plate and incubated at 37° C. for 1 hour. After incubation, unattached cells were removed by rinsing the plates twice with PBS. Attached cells were fixed with 10% formalin for 15 minutes and then stained with 0.5% crystal violet for 1 hour. The plates were gently washed three times with DDW and the contents of each well were solubilized in SDS for 5 minutes. The absorbance was measured at 570 nm with a microplate reader (BioRad). Similar cell attachment assays were performed with the VnP-16 motif (9.1 µg/cm$^2$) and NHEKs (passage 2), NHOKs (passage 2), NHDFs (passage 4), NHOFs (passage 4), PC-12, MC3T3-E1, CV-1, or NIH/3T3 cells. For cell spreading assays, cells ($3\times10^4$ cells/250 µL) were added to each substrate-coated plate and incubated at 37° C. for 3 hours. Attached cells were fixed with 10% formalin and then stained with 0.5% crystal violet for 1 hour. Plates were gently washed three times with PBS. Cell spreading was assessed by measuring the surface areas of the cells with Image-Pro Plus software (Version 4.5; Media Cybernetics).

Example 7. Cell Viability Assay

The viability of human osteogenic cells was analyzed using the EZ-Cytox cell viability assay kit (water-soluble tetrazolium salt (WST) assay; Daeillab). Osteogenic cells ($3\times10^3$ cells/100 µL) were seeded on a 96-well microplate, adapted for 48 hours, and treated with 50 µg/mL, 100 µg/mL, or 200 µg/mL of VnP-16 at 37° C. for 24 hours or 48 hours. The WST reagent solution (10 µL) was added to each well of the 96-well microplate containing 100 µL of cells. The plate was incubated at 37° C. for 2 hours. The absorbance was measured at 450 nm using a microplate reader (BioRad).

Example 8. Adhesion Inhibition Assay

Cells ($5\times10^4$ cells/250 µL) were preincubated with 5 mM EDTA, 500 µM MnCl$_2$, 100 µg/mL heparin, and 10 µg/mL function-blocking antibodies against integrin α1 (FB12), α2 (P1E6), α3 (P1B5), α4 (P4C2), α5 (P1D6), α6 (NKI-GoH3), β3 (B3A; Chemicon), αv (AV1), β1 (6S6; Millipore), or β3 (B3A) subunits at 37° C. for 15 minutes. Preincubated cells were transferred to plates precoated with VnP-16 (9.1 µg/cm$^2$) and incubated at 37° C. for 1 hour. The attached cells were quantified as described in Example 6.

Example 9. Pulldown Assay

Pulldown assays were performed using a biotinylated VnP-16 peptide according to a known method (Bottcher, R. T., *Bio protocol* 3, e962 (2013)). Cells were detached with trypsin/EDTA and resuspended in serum-free culture medium containing 0.1% BSA. Cells ($3\times10^6$) were seeded onto 100 mm culture dishes coated with biotin-conjugated VnP-16 peptides, incubated for 3 hours, and washed twice with cold PBS. The cells were scraped with 500 µL lysis buffer (50 mM Tris-HCl, pH 7.5, 150 mM NaCl, 0.1% Na-deoxycholate, 1% Triton X-100, protease, and phosphatase inhibitor cocktail tablets) followed by passing the lysates 15 times through a 26.5-gauge needle and centrifuging at 17,000×g for 10 minutes at 4° C. The supernatants of the cell lysates were incubated with 60 µL of streptavidin-agarose beads (Thermo Fisher Scientific, Waltham, Mass.) and centrifuged at 1,500×g for 2 minutes at 4° C. After washing the beads four times with lysis buffer, the precipitated proteins were resolved by 8% SDS-PAGE and analyzed by immunoblotting.

Example 10. Histological Staining of Osteogenic Cells

To visualize mineral deposits, cells were fixed with cold 95% ethanol for 30 minutes at −20° C. for 30 minutes and stained with 40 mM Alizarin red S solution (pH 4.2) for 1 hour. The stained cells were washed five times with DDW and rinsed with PBS for 15 minutes.

Example 11. RT-PCR and qRT-PCR

The mRNA levels of specific marker genes were determined by quantitative real-time PCR (qRT-PCR). Total RNA was isolated using the RNeasy® Mini Kit (Qiagen) according to the manufacturer's instructions. The RNA was denatured by incubating at 70° C. for 10 minutes and was kept on ice for 5 minutes. cDNA was prepared using reverse transcriptase (Invitrogen) and a random hexamer, and then used as a PCR amplicon of specific marker genes by using each primer at the final concentration of 300 nM (Table 1) and the quantity of cDNA corresponding to 133 ng of total RNA. After incubating the cDNA at 95° C. for 2 minutes, PCR was performed for 30 cycles at 95° C. for 20 seconds, 60° C. for 10 seconds, and 70° C. for 4 seconds. The reaction products were analyzed by 1.5% agarose gel electrophoresis and visualized by staining with ethidium bromide. The primers used in the PCR are summarized in Table 2 below.

TABLE 2

Primers for specific marker genes used to assess cell differentiation in RT-PCR and qRT-PCR

| Gene (NCBI ID) | Forward Primer | Reverse Primer | Product Size (bp) |
|---|---|---|---|
| ALP (NM_000478.3) | 5'-CCCACGTCGATTGCATCTCT-3' (SEQ ID NO: 1) | 5'-AGTAAGGCAGGTGCCAATGG-3' (SEQ ID NO: 2) | 100 |
| UNX2 (NM_001024630.1) | 5'-GCCTTCAAGGTGGTAGCCC-3' (SEQ ID NO: 3) | 5'-CGTTACCCGCCATGACAGTA-3' (SEQ ID NO: 4) | 67 |
| Bone sialoprotein (NM_004967.3) | 5'-AAGGCTACGATGGCTATGATGGT-3' (SEQ ID NO: 5) | 5'-AATGGTAGCCGGATGCAAAG-3' (SEQ ID NO: 6) | 100 |
| Osteocalcin (NM_199173.3) | 5'-GAAGCCCAGCGGTGCA-3' (SEQ ID NO: 7) | 5'-CACTACCTCGCTGCCCTCC-3' (SEQ ID NO: 8) | 70 |
| GAPDH (NM_002046.3) | 5'-CCATCTTCCAGGAGCGAGATC-3' (SEQ ID NO: 9) | 5'-GCCTTCTCCATGGTGGTGAA-3' (SEQ ID NO: 10) | 100 |

The qRT-PCR was performed using the 7500 Real-Time PCR System (Applied Biosystems). Primer sequences were designed using Primer Express® Software version 3.0 (Applied Biosystems). The cDNA was prepared using reverse transcriptase and a random hexamer and used for qRT-PCR amplification. The qRT-PCR was performed using SYBR® Premix Ex Taq™ (Takara) that contained a final concentration of 200 nM for each primer (Table 1) and a quantity of cDNA corresponding to 33 ng of total RNA. After incubation at 95° C. for 30 seconds, PCR was performed for 40 cycles at 95° C. for 15 seconds, 60° C. for 20 seconds, and 72° C. for 34 seconds. To analyze the data, cycle threshold values were determined by automated threshold analysis with Sequenced Detection Software version 1.3 (Applied Biosystems) and then the calculated cycle threshold values were exported to Microsoft Excel for analysis. The relative expression of each target mRNA was calculated using the comparative cycle threshold method according to the manufacturer's procedures (Applied Biosystems).

Example 12. FAK Phosphorylation Assay and Western Blotting

Human osteogenic cells (1×10$^6$) were plated on 60 mm dishes precoated with vitronectin (1 µg/mL) or synthetic peptides (50 µg/mL) and allowed to adhere for 3 hours. The cells were washed with cold PBS and lysed with 150 µL RIPA buffer (50 mM Tris-HCl, pH 7.4, 150 mM NaCl, 1 mM EDTA, 1% Triton X-100, 1 mM PMSF, 2 mM Na$_3$VO$_4$, and 1 mM glycerol phosphate) containing a protease inhibitor. The proteins present in the RIPA lysates were denatured using SDS sample buffer, resolved by SDS-PAGE, and electroblotted onto nitrocellulose membranes. The membranes were immunoblotted with primary antibodies against FAK (Upstate Biotechnology), FAK[pY$^{397}$], [pY$^{407}$], [pY$^{576}$], [pY$^{577}$], and [Y$^{861}$] (Invitrogen), or actin (Sigma-Aldrich). All blots were then incubated with anti-rabbit horseradish peroxidase-conjugated secondary antibodies (Cell Signaling Technology). Signals were detected by electrochemiluminescence (iNtRON Biotechnology).

Example 13. Transfection siRNA against human FAK (Sigma-Aldrich) or β1 integrin (Santa Cruz Biotechnology), and nonspecific control siRNAs (Invitrogen) were used for gene silencing. Human osteogenic cells were plated at a density of 1.5×10$^5$ cells per 100 mm dish, cultured for 1 day, and transfected with 10 nM, 50 nM, or 100 nM FAK siRNA or 100 nM control siRNA, or with 10 nM β1 integrin siRNA or 10 nM control siRNA using 15 µL of Lipofectamine™ RNAiMAX transfection reagent (Invitrogen). After 3 days, the transfected cells were harvested and analyzed by western blotting and cell attachment assays as described above.

Example 14. TRAP Staining

The TRAP assay was performed using the Leukocyte Acid Phosphatase Assay Kit (Sigma-Aldrich). The cells in culture were washed, fixed with 10% formalin, and stained with 40 mM sodium tartrate. TRAP-positive multinucleated cells containing more than three nuclei were considered osteoclasts.

Example 15. Bone Resorption Assay

Mature osteoclasts were prepared from the co-culture of bone marrow cells and primary osteoblasts on collagen gel-coated culture dishes as explained in the reference (Lee, J. H., et al., J. Biol. Chem., 284, 13725 to 13734 (2009)). For the bone resorption assay, the mature osteoclasts were cultured on Osteo Assay Surface plates precoated with vehicle (DMSO), vitronectin (0.23 µg/cm$^2$), or synthetic peptides (9.1 µg/cm$^2$) in the presence of M-CSF (30 ng/mL) and RANKL (100 ng/mL) for 6 days or 12 hours, respectively. The cells were removed using 10% Clorox (0.56% NaOCl), and the resorbed pits were photographed and analyzed using the Image Pro-Plus program (version 4.0, Media Cybernetics).

Example 16. Animal Experiments

For critical-size calvarial defects, 8-week-old male Sprague-Dawley rats (n=5 rats/group) were used. VnP-16 was dissolved in DDW and SP in DMSO (5 mg/mL) and then diluted with DDW. Absorbable collagen sponges (Bioland) were loaded with human recombinant BMP-2 (4 µg/cm$^2$, 15 µL volume; PeproTech), synthetic peptides (1 mg/cm² and 2 mg/cm², 15 μL volume), or vehicle (10 μL of DMSO and 5 μL of DDW). The surgical procedures for the creation of an 8 mm circular defect in the parietal bone and implantation of the collagen sponge were performed as described in the reference (Lee, J. H., et al., *Biomaterials*, 31, 3512 to 3519 (2010)). The rats were euthanized at 2 weeks after surgery, and whole calvaria were fixed in 4% paraformaldehyde at 4° C. for 24 hours and analyzed by μCT scanning. Details for the μCT scans are illustrated below.

For histomorphometric analysis, the specimens were decalcified with 12% EDTA for 4 weeks and embedded in paraffin. The paraffin-embedded samples were sectioned at a thickness of 4 μm and stained with Masson's trichrome. To examine the effects of VnP-16 on IL-1-induced mouse calvarial bone loss, dried collagen sponges loaded with vehicle (DMSO), IL-1 (2 μg), synthetic peptides (SP and VnP-16; 125 μg), or synthetic peptides in conjunction with IL-1 were implanted over the calvarial bones of 5-week-old male ICR mice (n=5 per group). The mice were sacrificed on day 7, and the whole calvariae were dissected, cleaned of soft tissue, fixed in 4% paraformaldehyde at 4° C. for 24 hours, subjected to TRAP staining, and then analyzed by μCT scanning. μCT was performed with the Micro-CT Skyscan 1172 system (70 kV, 141 μA, and 38 minutes integration time; Skyscan). Scans were integrated into 3D voxel images (2000×1048 pixel matrices). Bone images were reconstructed by the NRecon version 1.6.9.8 program (Bruker-microCT). Blue pseudo color was overlaid on the μCT images to clarify the eroded surface of calvarial bones. The regenerated bone volume and bone mineral content were calculated with CT Analyser version 1.14.4.1 (Bruker-microCT). Bone recovery rate (%) and calvarial thickness (mm) were calculated with CT Analyser version 1.14.4.1 according to standardized protocols. Hematoxylin and eosin and TRAP staining were performed with 5 μm paraffin sections. The percentage of osteoclast surface and the osteoclast number were calculated with OsteoMeasure XP Version 1.01 (OsteoMetrics) according to standardized protocols. All of the animal procedures were reviewed and approved by the Animal Care Committee of the Institute of Laboratory Animal Resources of Seoul National University.

Example 17. Measurement of Size

Osteoclast sizes were obtained by measuring the diameter of multinucleated, TRAP-positive cells on 40× photomicrographs taken using an Olympus BX51 microscope with a DP72 CCD camera and the CellSens Dimension (version 1.6) analysis system. Cell size was expressed as the average diameter ±S.D. of the 20 largest cells found on four photomicrographs.

Example 18. Statistical Analyses

All of the data are presented as mean±S.D. The statistical analyses of data were performed using the STATISTICA 6.0 software package (StatSoft). The results were compared using analysis of variance tests. When significant differences were found, pairwise comparisons were performed using Scheffe's adjustment. Statistical significance was calculated using a two-tailed Student's t-test. Differences with a P value of less than 0.05 were considered statistically significant.

Example 19. Construction, Expression, and Purification of Human Vitronectin Truncations Human vitronectin cDNA was cloned by RT-PCR using Superscript II reverse transcriptase. For the template, mRNA isolated from Hep G2 cells was used. All of the three truncations of human vitronectin (Vn-FI, Vn-FII, and Vn-FIII) were amplified by PCR using vitronectin cDNA as a template and subsequently subcloned into the pGEM-T Easy vector (Promega). The primers used in the PCR are summarized in Table 3 below.

TABLE 3

Primers used in RT-PCR for amplification of three truncations

| Truncations | Sense Primer | Antisense Primer |
|---|---|---|
| Vn-FI | 5'-GGATCCGACCAAGAGTCATG CAAG-3' (SEQ ID NO: 11) | 5'-GAATTCTCAGGGCTGAGGTCTCC-3' (SEQ ID NO: 12) |
| Vn-FII | 5'-GGATCCCCAGCAGAGGAGGA GC-3' (SEQ ID NO: 13) | 5'-GAATTCTCACCAGAAGAGAAGCT CGAAG-3' (SEQ ID NO: 14) |
| Vn-FIII | 5'-GGATCCGGCAGAACCTCTG-3' (SEQ ID NO: 15) | 5'-GAATTCTCACAGATGGCCAGGAG CTG-3' (SEQ ID NO: 16) |

The resultant truncations were liberated with the appropriate restriction enzymes and subsequently cloned into the BamHI and EcoRI sites of an appropriate bacterial expression plasmid vector. μCT-32a(+) (for rVn-FI and rVn-FIII; Novagen), pRSET (for rVn-FII; Invitrogen) or both were used for recombinant expression. Correct insert orientation was verified by DNA sequence analysis. The recombinant expression and purification of truncated versions of vitronectin, including truncations I (rVn-FI), rVn-FII, and rVn-FIII, were performed as previously described in the reference (Kim, J. M., et al., Exp. Cell. Res., 304, 317 to 327 (2005)). Briefly, the expression of recombinant proteins in *E. coli* cells (BL21 strain) was induced with 1 mM isopropyl-β-D-thiogalactopyranoside at 37° C. for 5 hours. After protein induction, cells were harvested by centrifugation at 6,000×g for 10 minutes. Cell pellets were resuspended in lysis buffer (50 mM $NaH_2PO_4$ and 300 mM NaCl, pH 8.0, for rVn-FI; and 8 M urea, 10 mM Tris-HCl, pH 8.0, 100 mM $NaH_2PO_4$, and 1 mM phenylmethylsulfonyl fluoride (PMSF) for rVn-FII and rVn-FIII). Recombinant rVn-FI was purified using a $Ni^{2+}$-NTA-agarose column (Qiagen). Purified recombinant $His_6$-tagged truncations (rVn-FII and rVn-FIII) were further dialyzed sequentially into 3 M, 2 M, 1 M, and 0.5 M urea at pH 3.0. Finally, these proteins were dialyzed in PBS (pH 3.0) containing 1 mM PMSF. Protein concentrations were determined with the Bradford reagent (BioRad).

Example 20. Circular Dichroism (CD) Spectroscopy

Recombinant rVn proteins were prepared in PBS and diluted to 0.2 mg/mL. CD spectra were recorded on a Jasco spectropolarimeter (Model J-715; Jasco International). Protein samples were analyzed at 23° C. from 180 nm to 300 nm with a 2 mm cell path length. Three repetitive scans were averaged and smoothed by binomial curve filtering. Molar ellipticities (in degrees·cm$^2$·dmol$^{-1}$) were calculated according to the protein concentration and molar mass of each rVn protein.

Example 21. Cell Migration Assay

Cell migration assays were performed with transwell migration chambers (pore size, 8 μm; Corning). The lower side of each transwell filter was coated with vitronectin (0.23 μg/cm$^2$) or with rVn-FI, rVn-FII, or rVn-FIII (5.7 μg/cm$^2$) at 4° C. for 18 hours and then blocked with 1% BSA in PBS at 37° C. for 1 hour. Cells (2×10$^5$ cells/mL) were resuspended in DMEM containing 0.5% FBS and 0.1% BSA. This suspension (100 μL) was seeded in the upper chamber of a transwell filter. After seeding the cell lysate (100 μL) to the upper chamber of the transwell migration chambers, the cells were allowed to migrate at 37° C. for 24 hours. Cells were then fixed with 10% formalin for 15 minutes and stained with 0.5% crystal violet. Unmigrated cells, those remaining in the upper side of the transwell filter, were removed with a cotton swab and counted under light microscopy. Cell migration was quantified by counting the number of cells that had migrated through the filter.

Example 22. Flow Cytometry

SKP-derived mesenchymal cells were detached by trypsinization, and aliquots of 1.0×10$^6$ cells were prepared in 5 mL round-bottom test tubes. After rinsing with PBS containing 0.2% FBS, the cells were centrifuged and blocked with PBS containing 1% BSA and 0.2% FBS at 4° C. for 30 minutes. The cells were incubated with primary antibodies to CD29 (1:50; Chemicon), CD44 (1:25; BD Pharmingen), CD73 (1:40; BD Pharmingen), CD133 (1:50; Abcam), CD146 (1:1000; Abcam), and Stro-1 (1:17; Santa Cruz Biotechnology) on ice for 1 hour. After washing with PBS containing 0.2% FBS, the cells were incubated with fluorescein isothiocyanate-labeled secondary antibodies on ice for 1 hour. Finally, the cells were analyzed on a FACSCalibur flow cytometer (Becton-Dickinson).

The details confirmed by the Examples above are summarized in the following Experimental Examples.

Experimental Example 1. RVYFFKGKQYWE (SEQ ID NO: 17) Motif as Cell-Binding Sequence for Fibroblast-Lineage Cells To identify the biologically active domains conferring cell functions exerted by vitronectin, three constructs were generated to recombinantly express the human vitronectin truncations of interest (rVn-FI, rVn-FII, and rVn-FIII). The corresponding vitronectin truncations were separately expressed in *E. coli*, and characterization and cell functions of the expressed rVn truncations were presented in FIGS. 7 and 8, respectively. Although rVn-FII exhibited lower cell attachment activity compared to that of rVn-FI (FIGS. 8a and 8b), the present inventors have focused on identifying the bioactive cell binding sequences required for the activity of rVn-FII because peptides lacking the RGD motif within the rVn-FI do not have cell functions.

Figure 1A:
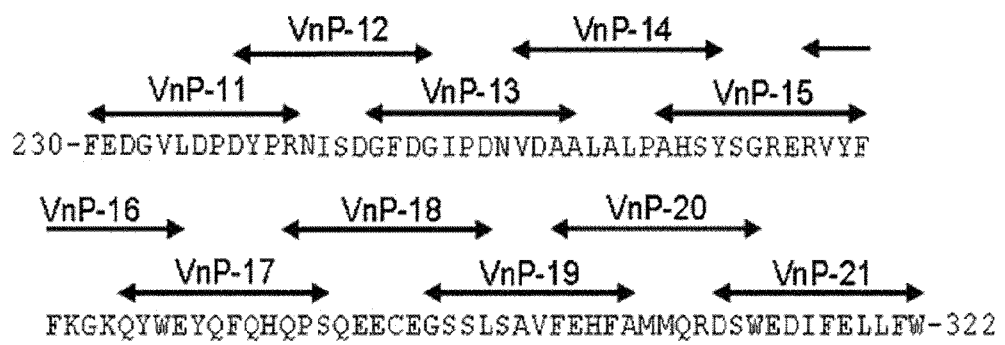
FIGS. 1a to 1g show drawings which confirm that a VnP-16 dodecapeptide with two β-strands promotes cell functions in fibroblast-lineage cells.
Figure 1B:
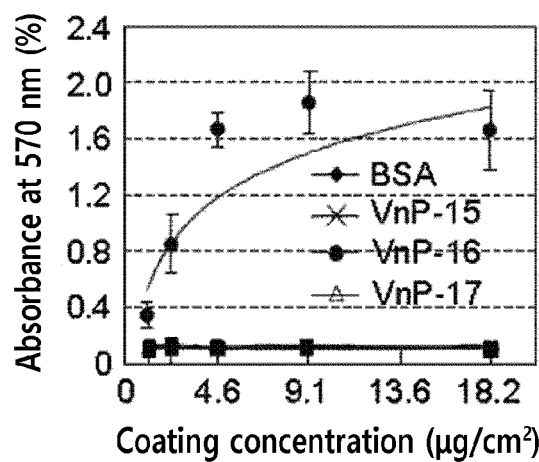
Figure 1C:
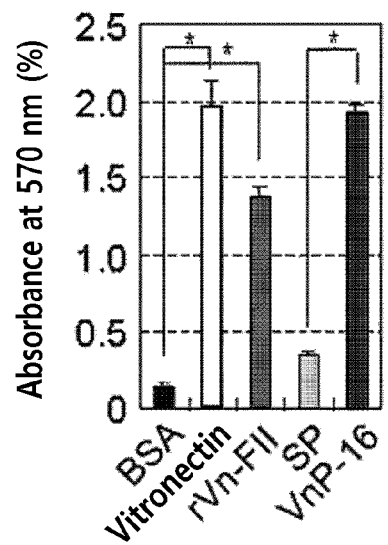

Since the rVn-FII truncation consists of a long (173 residues in length) polypeptide chain and contains four β-strands from the computational structure prediction (FIG. 9), 11 overlapping 12-mer peptides covering amino acids at positions 230 to 322 of rVn-FII were synthesized (FIG. 1a). In particular, human osteogenic cells were used to test both cell functions and osteoinductive activity of recombinant vitronectin truncations and synthetic peptides. For the preparation of osteogenic cells, skin-derived precursors (SKPs) were isolated from human foreskin and subjected to directed differentiation to mesenchymal cells to osteogenic cells (FIG. 10). As shown in FIGS. 1b and 1c, VnP-16 (RVYFFKGKQYWE (SEQ ID NO: 17), residues at positions 270 to 281) significantly promoted the cell attachment activity of osteogenic cells in a dose-dependent manner, and the cell attachment activity of VnP-16 reached a maximum level of about 9.1 μg/cm$^2$.

Figure 1D:
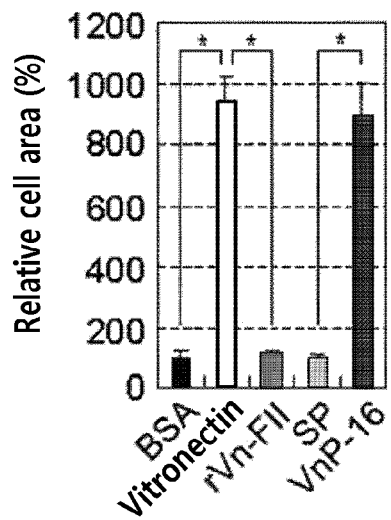
Figure 1E:
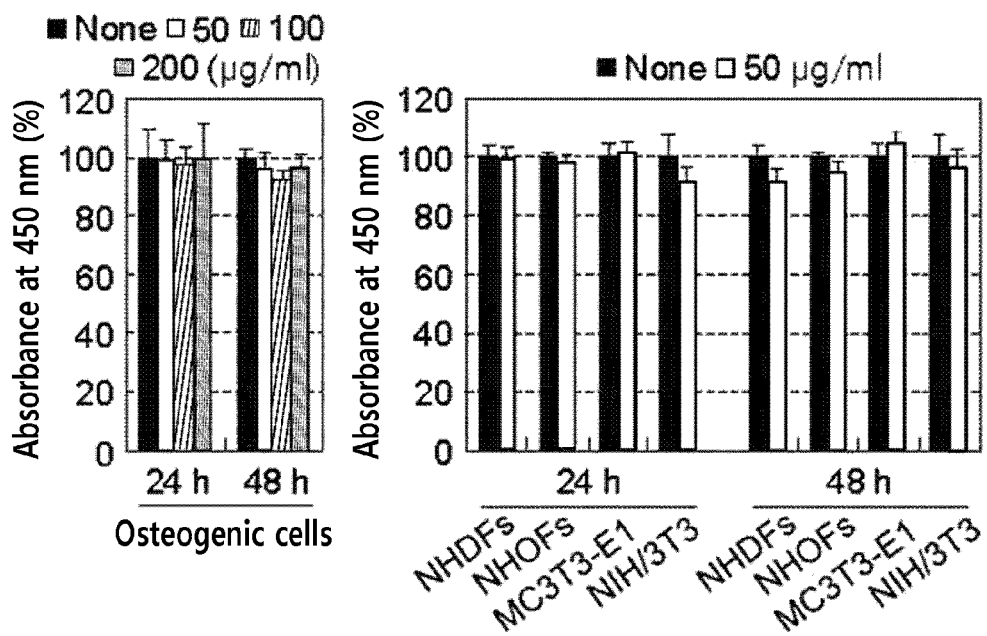
Figure 1F:
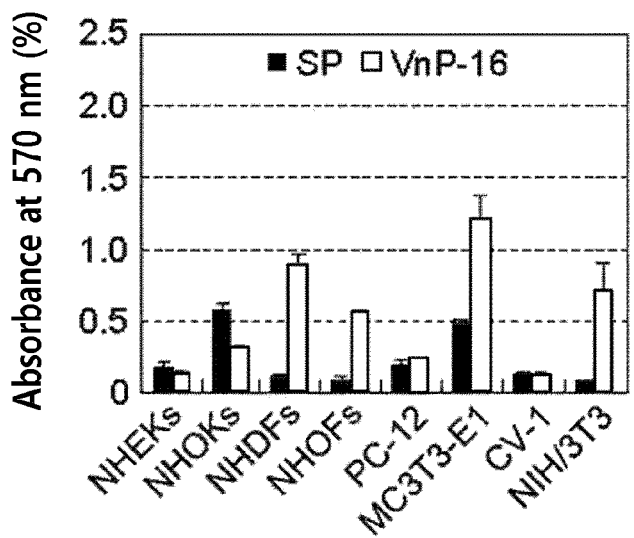

Additionally, VnP-16 induced cell spreading to an extent comparable to vitronectin, whereas scrambled peptide (SP) was ineffective in promoting cell spreading (FIG. 1d). Additionally, VnP-16 did not affect the viability of cells or cell lines tested (FIG. 1e) and the result confirmed that VnP-16 is cytocompatible without compromising cell viability. Since VnP-16 exhibited cell attachment activity in osteogenic cells, the present inventors have further examined whether VnP-16 could also mediate attachment of other types of cells. Interestingly, VnP-16 displayed cell attachment activity only to primary fibroblasts, including normal human dermal fibroblasts (NHDFs) and normal human oral fibroblasts (NHOFs), and to fibroblast-lineage cells, including MC3T3-E1 and NIH/3T3 cells (FIG. 1f). This result demonstrated that VnP-16 acts via a fibroblast-lineage-specific attachment mechanism.

Figure 1G:
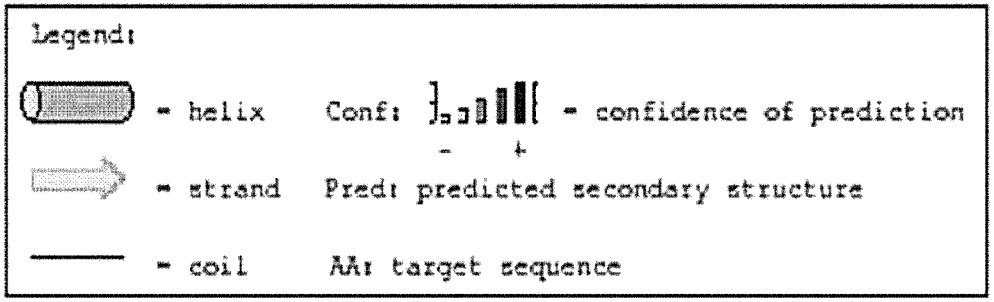

Then, the folding of VnP-16 was predicted using the PSIPRED protein structure prediction server (bioinfcs.ucl.ac.uk/psipred/). Computation for the VnP-16 dodecapeptide structure predicted that VnP-16 has two β-strands (FIG. 1g). From these result it was confirmed that VnP-16 having a secondary structure is a bioactive cell binding sequence acting in fibroblast-lineage cells, but not in keratinocytes.

Experimental Example 2. β1 Integrin Mediating VnP-16-Induced Cell Function

In this Experimental Example, it was examined that which specific adhesion receptor for VnP-16 mediates cell attachment in osteogenic cells. As a result, it was confirmed that cell attachment to VnP-16 was not inhibited by heparin (FIG. 2a), suggesting that the cell surface proteoglycan receptor is not the receptor for VnP-16.

Since the binding of integrins and α-dystroglycan to their ligands requires a divalent cation, such as $Ca^{2+}$ or $Mn^{2+}$, the effect of EDTA (i.e., a metal-chelating reagent) on cell attachment to VnP-16 was examined. As a result, it was confirmed that the cell attachment was completely inhibited in osteogenic cells pretreated with EDTA compared with control cells. In contrast, treatment with $Mn^{2+}$ significantly enhanced cell attachment (FIG. 2a).

Additionally, the effects of integrin subunit-blocking antibodies on cell attachment to VnP-16 were also examined. Cell attachment was almost completely inhibited by treatment with a β1-blocking antibody (clone 6S6; FIG. 2b). Although β3 integrin plays a key role in cell attachment and migration, β3 integrin was not involved in the VnP-16-mediated attachment of osteogenic cells. Additionally, β1 integrin expressed by transfection of β1 integrin small interfering RNA (siRNA; FIG. 2c) significantly inhibited cell attachment to VnP-16 compared with control siRNA-transfected cells (FIG. 2d).

As such, to confirm whether VnP-16 directly binds to and activates cell surface β1 integrins, human osteogenic cells were cultured on culture dishes, in which osteogenic cells or HOS cells (i.e., a type of osteogenic cells) coated with biotinylated VnP-16, for 3 hours and subsequently subjected to a pulldown assay selectively with streptavidin beads and immunoblotting, and then the level of β1 integrin was measured. As a result, as shown in the results with regard to the pulldown assay in FIG. 2e, it was confirmed that β1 integrin did not bind to streptavidin beads alone but was selectively bound to biotinylated VnP-16, in both cell lines. From these results, it was confirmed that β1 integrin functions as a major surface receptor for VnP-16 in osteogenic cells.

Experimental Example 3. Focal Adhesion Kinase (FAK) Activation Essential for VnP-16-Mediated Signaling and Osteoblast Differentiation To investigate the downstream signaling pathways activated by VnP-16/β1 integrin-mediated cell functions in osteogenic cells, it was examined whether the binding of cells to VnP-16 is due to FAK activation.

The levels of FAK phosphorylation at Tyr397 following the VnP-16-mediated attachment and spreading of osteogenic cells were evidently increased compared with vehicle- or SP-treated control. In contrast, the levels of phospho-FAK Tyr-407, -576, -577, and -861 remained at basal levels (FIG. 2f).

Since FAK Tyr397 is an autophosphorylation site that promotes interaction with c-Src or Fyn, the expression of phospho-c-Src was also tested. The levels of phospho-c-Src Tyr416 evidently increased compared with vehicle- or SP-treated control, but not in the phospho-Akt Ser473 and phospho-PKCδ Thr505 (FIG. 2f) suggesting that FAK phosphorylation at Tyr397 and c-Src phosphorylation at Tyr416 are linked to VnP-16/β1 integrin-mediated signaling. Further, cell attachment to VnP-16 after suppression of FAK phosphorylation at Tyr397 by pretreatment of PF-573228 (i.e., a FAK inhibitor that effectively blocks FAK phosphorylation at Tyr397) was significantly inhibited in a dose-dependent manner (FIGS. 2g and 2h).

Figure 2J:
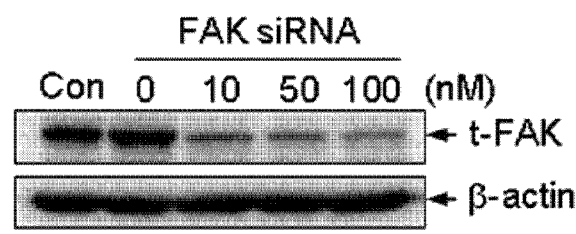
Figure 2K:
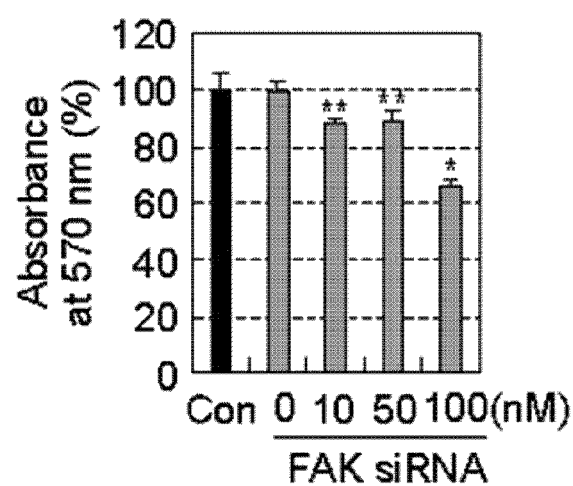

Then, to investigate the role of FAK phosphorylation at Tyr397 on osteoblast differentiation, osteoblast precursors and osteogenic cells were cultured onto VnP-16-treated plates in osteogenic differentiation medium containing PF-573228. PF-573228 reduced calcium deposition, and simultaneously, notably weakened alkaline phosphatase (ALP) activity in the tested osteoblast precursors (FIG. 2i). These results indicate that the suppression of FAK phosphorylation at Tyr397 by PF-573228 pretreatment inhibits osteoblast differentiation. Additionally, it was confirmed that PF-573228 did not affect cell growth at the concentrations and incubation time used in the present invention, excluding the possibility that the PF-573228-mediated inhibition of cell attachment to VnP-16 is caused by general cytotoxicity. Further, the suppression of FAK expression in the FAK siRNA-transfected cells significantly inhibited cell attachment to VnP-16 compared with that in the control siRNA-transfected cells (FIGS. 2j and 2k). These results support that FAK phosphorylation at Tyr397 is essential for VnP-16/β1 integrin-mediated signaling and osteoblast differentiation.

Experimental Example 4. VnP-16 Promoting New Bone Formation

The effects of VnP-16 on osteogenic capacity to repair bone defects in vivo were examined using rat models with critical-size calvarial defects.

Figure 3A:
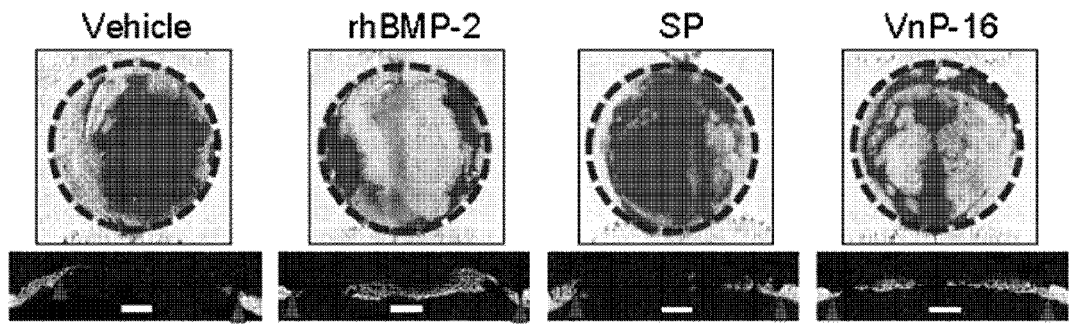
FIGS. 3a to 3e show the effects of VnP-16 on in vivo bone resorption. Critical-sized rat calvarial defects were implanted with absorbable collagen sponges treated with vehicle (DMSO), BMP-2 (2 μg/scaffold), scrambled peptide (SP; 1 mg/scaffold), or VnP-16 (1 mg/scaffold).
Figure 3B:
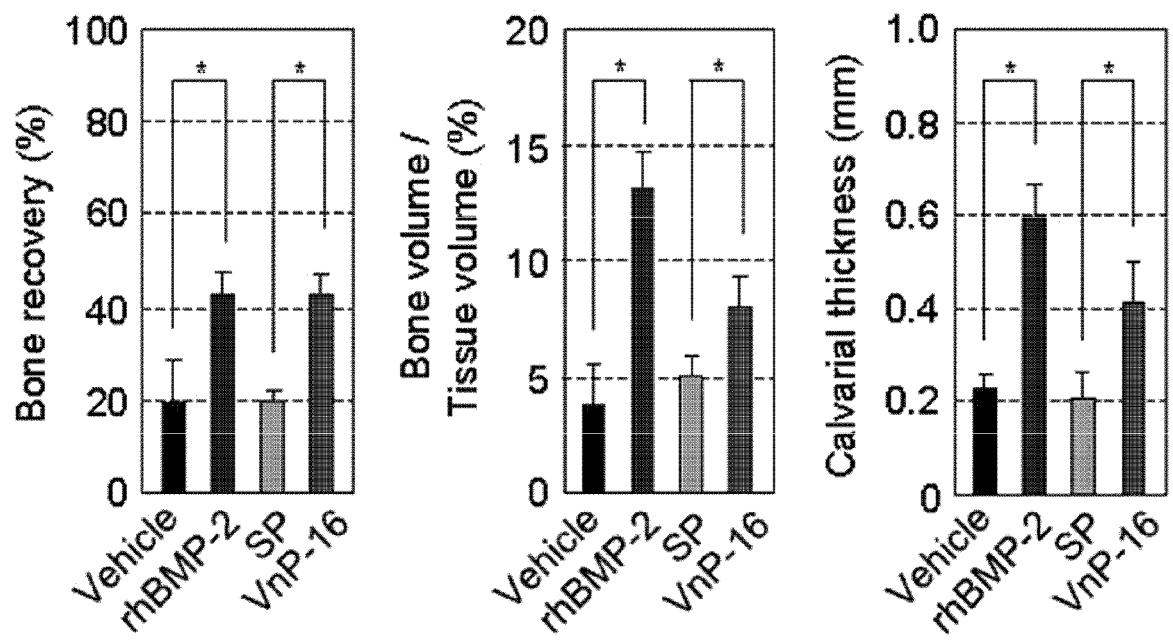
Figure 3C:
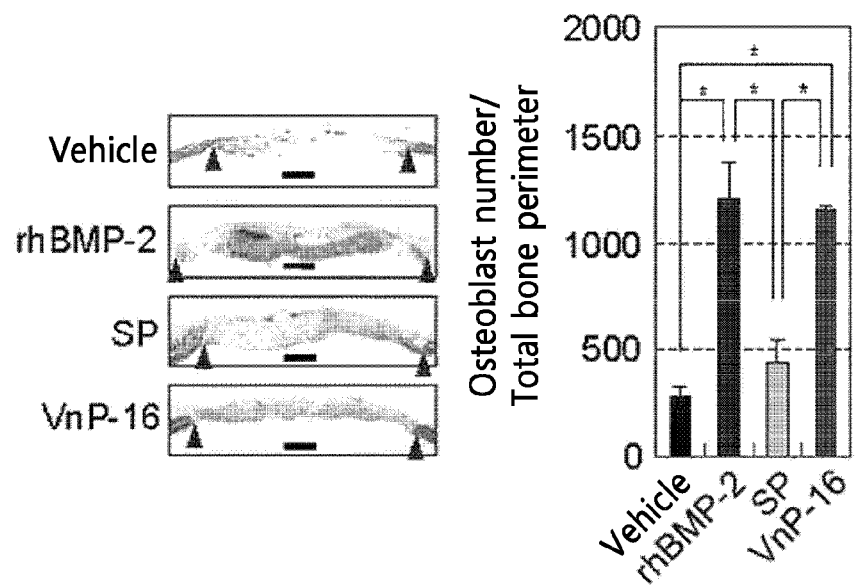
Figure 3D:
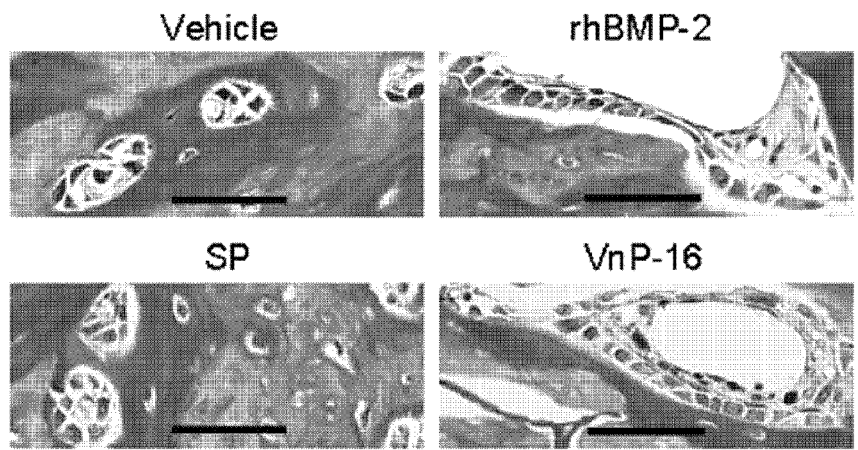

Micro-computed tomographic (μCT) images of calvarial defects demonstrated that the vehicle- and SP-treated control groups showed only limited new bone formation at the defect margins two weeks after surgery, whereas the VnP-16-treated group showed significant bone healing (FIG. 3a, top). Additionally, the amount of newly generated bone in the VnP-16-treated group was comparable with that in the bone morphogenetic protein 2 (BMP-2)-treated group. The other μCT images of calvarial defects (FIG. 3a, bottom), quantitative histomorphometry for calvarial volume and thickness (FIG. 3b), and Masson's trichrome-stained histological sections for collagen deposition (FIG. 3c left) confirmed that the amount of bone regeneration in the VnP-16-treated group is greater than those in the vehicle- and SP-treated control groups, which were mostly filled with fibrous connective tissues and/or degradation remnants of the absorbable collagen sponges used as scaffolds (FIG. 3c right).

Figure 3E:
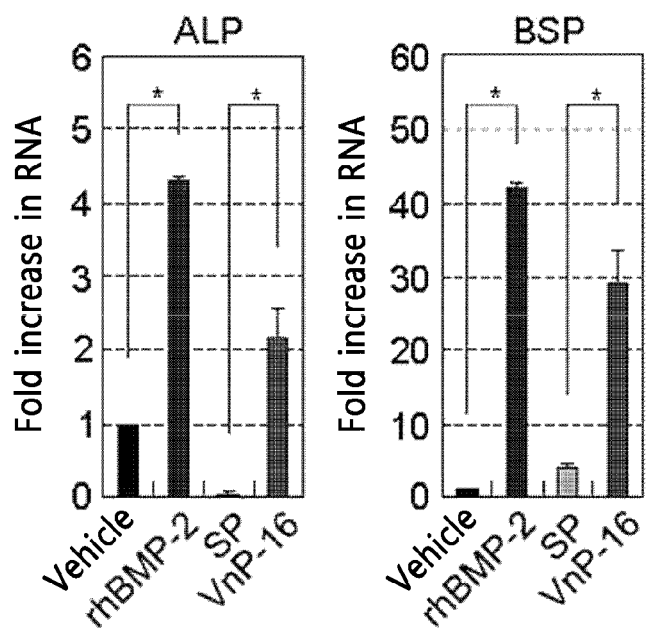

The presence of osteoblasts in the newly generated bone was detected using Masson's trichrome-stained histological sections. As a result, it was confirmed that the osteoblast number was significantly increased in the VnP-16-treated group compared to those of vehicle- or SP-treated control groups, and that the osteoblast number of the VnP-16-treated group was comparable to the expression level of the (BMP-2)-treated group (FIG. 3d). Further, it was confirmed that VnP-16-treated group exhibited significantly increased expression of osteogenic markers compared with the vehicle- and SP-treated control groups (FIG. 3e). This data demonstrates a strong anabolic effect of VnP-16 on bone formation by stimulating osteoblast differentiation.

Experimental Example 5. VnP-16 Restricting RANKL-Induced Osteoclast Differentiation Via Inhibition of JNK-c-Fos-NFATc1 Signaling Pathway It was examined whether VnP-16 could inhibit osteoclast differentiation via directly acting on osteoclast precursor cells. As a result, it was confirmed that M-CSF and RANKL induced numerous tartrate-resistant acid phosphatase (TRAP)-positive multinucleated osteoclasts from bone marrow-derived macrophage (BMMs; FIG. 4a). VnP-16 almost completely inhibited M-CSF and RANKL-induced osteoclastogenesis compared with the vehicle and SP control groups (FIGS. 4a to 4c). Additionally, VnP-16 also inhibited the F-actin mediated cytoskeletal organization (FIG. 4d).

Furthermore, the effects of VnP-16 on bone resorptive activity by osteoclasts were assessed. Through the images and measured areas of resorption pits photographed after removing osteoclasts, it was confirmed that VnP-16 also inhibits bone resorptive activity (FIGS. 4e and 4f).

Additionally, VnP-16 did not affect cell proliferation and viability of BMMs at the concentration (9.1 μg/cm$^2$) that blocks osteoclastogenesis (FIG. 4g), and from these results, it was confirmed that the inhibitory effect of VnP-16 was not due to cytotoxicity or cell proliferation.

To further assess the molecular mechanisms underlying the inhibitory effect of VnP-16 on M-CSF and RANKL-induced osteoclast differentiation, the expression levels of c-Fos and NFATc1, which are crucial and fundamental transcription factors for osteoclast differentiation, were examined. A lack of either of these two transcription factors leads to a defect in osteoclast development, and it was confirmed that the treatment of BMMs with VnP-16 suppressed M-CSF and RANKL-induced expressions of c-Fos and NFATc1 (FIG. 4h).

Therefore, to investigate how VnP-16 suppresses M-CSF and RANKL-induced c-Fos and NFATc1 expression, the effects of VnP-16 on the activation of mitogen-activated protein kinases (MAPKs) were examined. It is known that these RANK downstream signaling events are implicated in the expression of c-Fos and NFATc1 and osteoclast differentiation. VnP-16 did not affect basal Janus N-terminal kinase (JNK) levels, but VnP-16 obviously inhibited RANKL-stimulated JNK phosphorylation (FIG. 4i) and VnP-16 neither affected RANKL-induced Erk phosphorylation nor p38 phosphorylation (FIG. 4i). From these results, it was confirmed that VnP-16, which induces a negative control on osteoclast differentiation, suppressed JNK phosphorylation and also caused the decrease of the expressions of c-Fos and NFATc1.

Experimental Example 6. VnP-16 Preventing Src-PYK2 Signaling

The αvβ3 integrin-ligand occupancy activates c-Src by phosphorylating Tyr416, and the actin cytoskeleton is thereby organized. Additionally, the Src-PYK2 signaling by the engagement of Src and PYK2 with αvβ3 integrin is known to be related to the resorptive function of mature osteoclasts. PYK2 and Src are protein molecules essential for organizing the cytoskeleton of osteoclasts. The binding of ligands to αvβ3 integrin activates c-Src by phosphorylating Tyr416, and the actin cytoskeleton is thereby organized. Then, the binding between αvβ3 integrin and Src and PYK2 is involved in the resorptive function of mature osteoclasts. Since the average cell size of M-CSF and RANKL-induced osteoclasts was decreased by VnP-16 (FIG. 4c), the present inventors had suspected that αvβ3 integrin signaling might be associated with the inhibition of resorptive function of M-CSF and RANKL by VnP-16, and thus, they have examined the effect of VnP-16 with regard to the expression levels of the protein molecules associated with the αvβ3 integrin signaling.

Figure 5A:
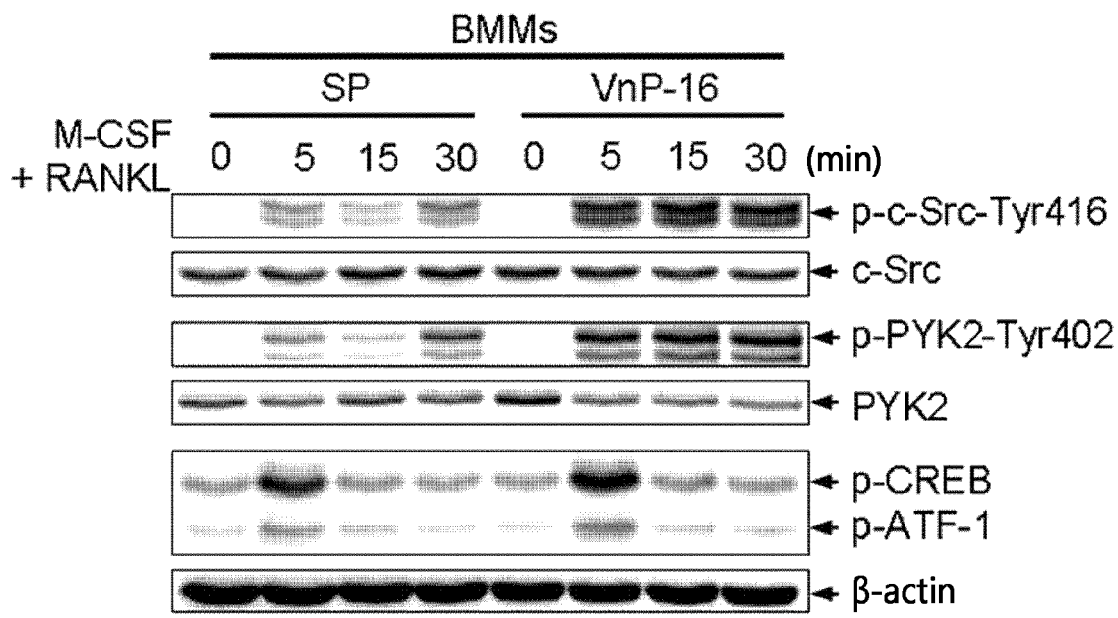
FIGS. 5a to 5e show the results with regard to the effects of VnP-16 on M-CSF and RANKL-induced activation of c-Src and PYK2 in (BMMs), preosteoclasts, and mature osteoclasts.
Figure 5B:
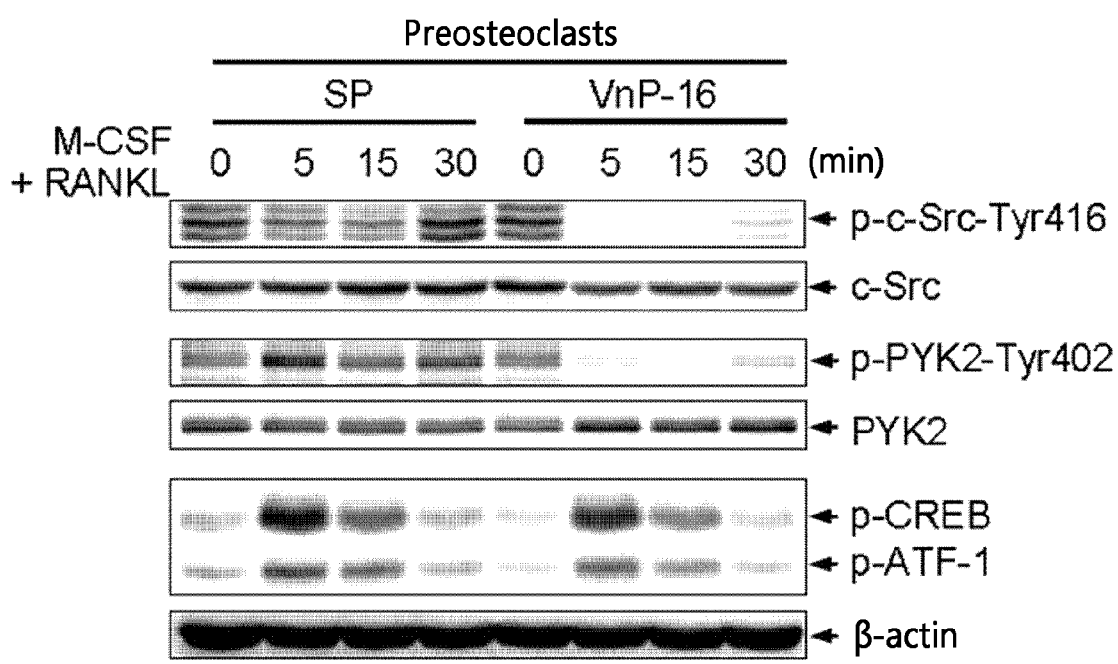
Figure 5C:
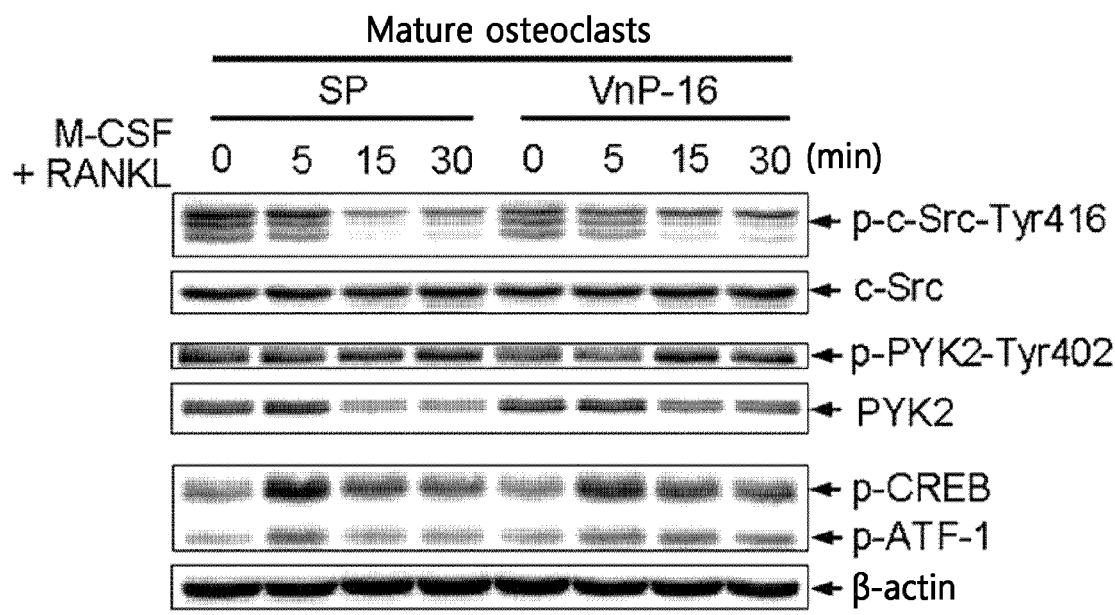
Figure 5D:
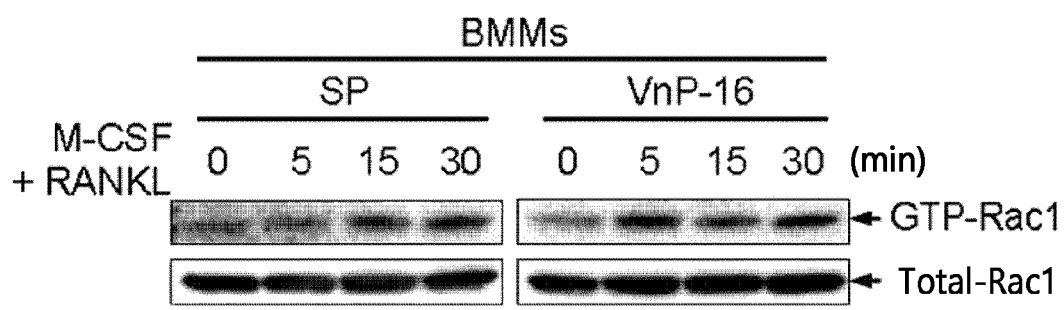
Figure 5E:
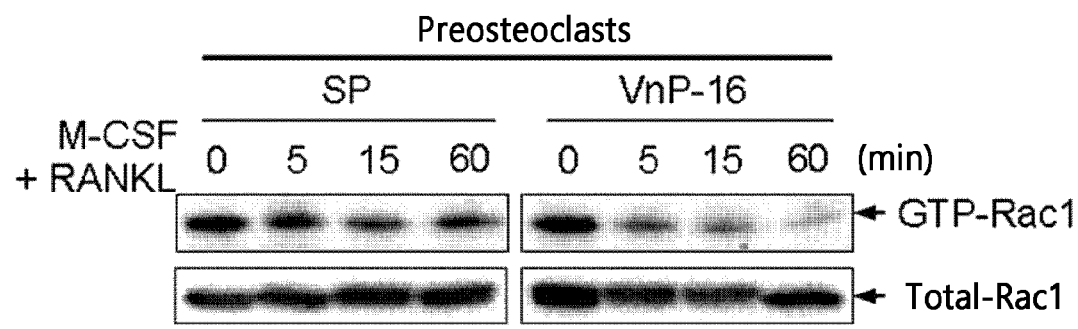

As a result, it was confirmed in BMMs that VnP-16 disturbs the phosphorylations of Src at Tyr416 and PYK2 at Tyr402 (FIG. 5a). Similarly, it was confirmed that VnP-16 inhibited and suppressed the phosphorylations of the proteins in preosteoclasts and mature osteoclasts, respectively (FIGS. 5b and 5c). Furthermore, it was confirmed that VnP-16 alters the level of GTP-bound Rac1, the final molecular effector of the αvβ3 integrin signaling, during M-CSF- and RANKL-induced osteoclastogenesis in BMMs (FIG. 5d). Unlike SP used as a control, VnP-16 inhibited the expression of GTP-bound Rac1 in preosteoclasts (FIG. 5e). From these results, it was confirmed that VnP-16 suppresses the expression of the protein molecules associated with the αvβ3 integrin signaling during M-CSF- and RANKL-induced bone resorption process, thereby inhibiting cytoskeletal organization in osteoclasts.

Experimental Example 7. VnP-16 Inhibiting Bone Resorption In Vitro and Preventing IL-1-Induced Bone Destruction In Vivo To assess the resorptive activity of preexisting osteoclasts in vitro, mature osteoclasts were cultured on Osteo Assay Surface plates, which were precoated with the vehicle, vitronectin, SP, or VnP-16, in the presence of RANKL and M-CSF. After 12 hours, many resorption pits caused by osteoclasts were generated; however, VnP-16 significantly inhibited the area of these pits (FIGS. 6a and 6b). After 24 hours, the effect of VnP-16 on the area of the resorption pits was similar to that on the resorption pits observed in the osteoclasts after culturing for 12 hours (FIGS. 12a and 12b). However, it was confirmed that VnP-16 had no effect on the viability of osteoclasts (FIG. 12c).

Figure 6F:
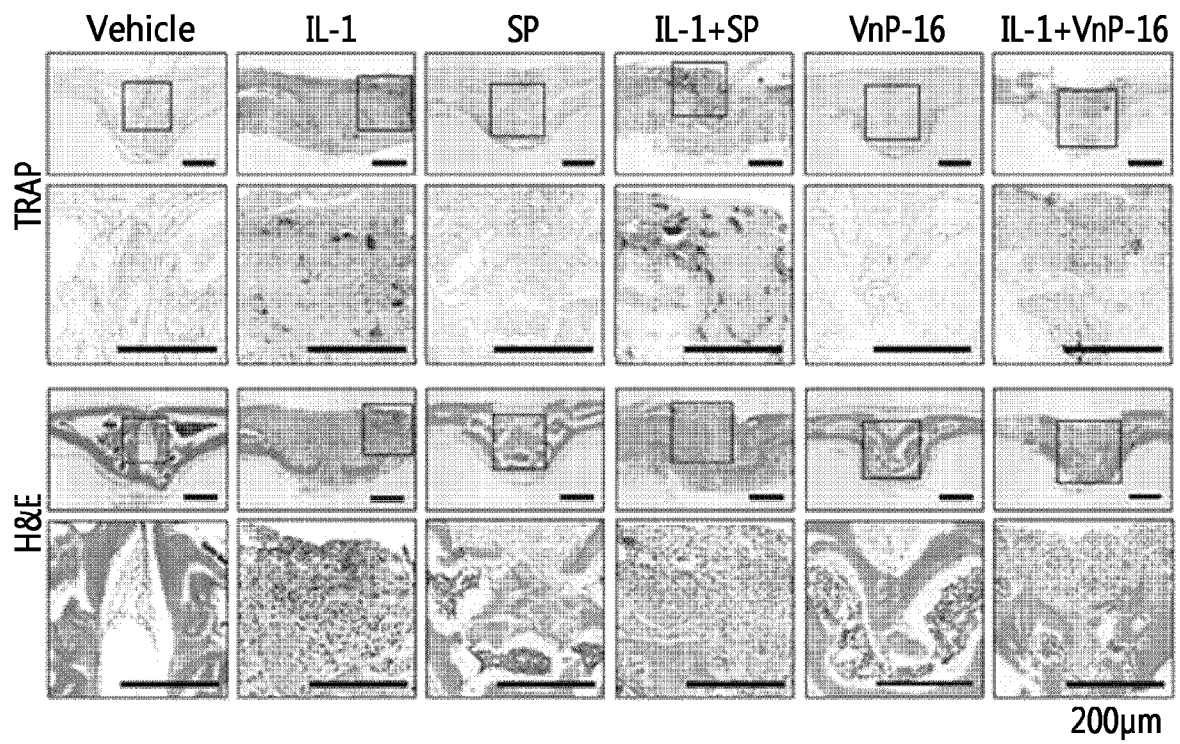
Figure 6G:
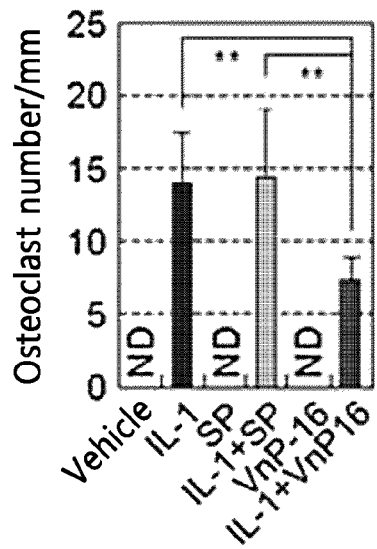
Figure 6H:
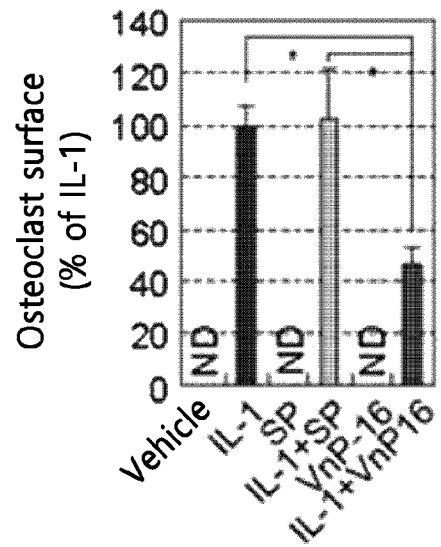

To confirm the biological potency of VnP-16 on bone resorption in vivo, the effects of VnP-16 on interleukin-1 (IL-1)-induced bone destruction in mice. As a result, it was confirmed based on the μCT images and TRAP staining of whole calvariae that IL-1 treatment can result in severe bone destruction (FIG. 6c). Compared with that in the group simultaneously treated with IL-1 and SP, bone destruction in the group simultaneously treated with IL-1 and VnP-16 was significantly lower (FIG. 6c). Furthermore, although IL-1 decreased bone volume and bone density, the group treated with VnP-16 certainly prevented the decrease of bone volume and bone density compared to the group treated with SP (FIGS. 6d and 6e). Additionally, histological and histomorphometric analyses of calvarial bones showed that IL-1 significantly increased the number of TRAP-positive osteoclasts and their surfaces; however, VnP-16 reduced these parameters induced by IL-1 (FIGS. 6f to 6h).

Experimental Example 8. Characteristics of rVn Truncations

To identify the cell functions exerted by different regions of human vitronectin and precisely define the biologically active sequences conferring these functional activities, three constructs were generated to recombinantly express the human vitronectin truncations of interest (rVn-FI to rVn-FIII). The coding sequences were cloned by RT-PCR using RNA obtained from the human hepatocellular carcinoma cell line Hep G2, and the corresponding vitronectin truncations were separately expressed in E. coli. A schematic diagram showing the rVn truncations of vitronectin, including the amino acid positions of their boundaries, is shown in FIG. 7a.

To provide convenient handles for subsequent protein purification and identification assays, all rVn truncations were expressed as histidine 6 ($His_6$)-tagged fusion proteins (FIG. 7b). All three rVn truncations were purified to near homogeneity with $Ni^i$-nitrilotriacetic acid (NTA) agarose under denaturing conditions, as determined by the Coomassie staining of an SDS-polyacrylamide gel (FIG. 7b). While rVn-FI was detected predominantly in the soluble fraction of the E. coli lysates, rVn-FII and rVn-FIII were mainly present in the insoluble fraction. Accordingly, rVn-FI was purified directly through $Ni^{2+}$-NTA affinity chromatography, whereas additional refolding processes were required for the purification of rVn-FII and rVn-FIII. The predicted molecular weights of rVn-FI, rVn-FII, and rVn-FIII were 32 kDa, 23 kDa, and 35 kDa, respectively; however, rVn-FI and rVn-FII migrated more slowly than expected for their predicted molecular weights (FIG. 7b). This finding was consistent with a previous study (Kamikubo, Y., Okumura, Y. &

Loskutoff, D. J., *J. Biol. Chem.*, 277, 27109 to 27119 (2002)), in which a significant difference between the predicted and observed mobility of an rVn truncation is disclosed. The actual size of the Vn1-97 truncation based on mass spectrometric data was 27,908 Da, although the Vn1-97 truncation migrated with a molecular weight of 42 kDa. This discrepancy was thought to occur due to many factors affecting protein migration, such as amino acid composition or an inconsistent charge-to-mass ratio in SDS-PAGE analysis. To determine whether the rVn truncations formed intramolecular disulfide bonds, the purified recombinant proteins were subjected to SDS-PAGE under a reducing or nonreducing condition and the presence of any difference in mobility was observed. The treatment of all three rVn truncations with 100 mM dithiothreitol prior to SDS-PAGE caused small but reproducible reductions in mobility, suggesting that intramolecular disulfide bonds were present in all three recombinant proteins (FIG. 7c).

Then, to assess the folding of the rVn truncations expressed in bacteria, their secondary structures were assessed by CD spectroscopy. The CD spectra of the $His_6$-rVn truncations showed ellipticity minimums at 208 nm, 212 nm, and 216 nm, respectively (FIG. 7d). These values are a characteristic of a protein which is rich in β-structure, suggesting that the rVn truncations expressed in bacteria are sufficiently folded and they could be able to reflect their proper cell functions.

Experimental Example 9. Cell Functions of rVn Truncations rVn

Since vitronectin is known to mediate cell attachment to various types of osteoblast-like cells, the cell attachment activity of each rVn truncation was examined.

Human osteogenic cells adhered to rVn-FI and rVn-FII in a dose-dependent manner but did not adhere to rVn-FIII. The cell attachment activity of rVn-FI and rVn-FII reached a maximum level at about 5.7 µg/cm$^2$ in osteogenic cells (FIG. 8a). Additionally, it was confirmed that human plasma vitronectin strongly promoted cell attachment (FIG. 8b), spreading (FIG. 8c), and migration (FIG. 8d) in osteogenic cells. Both rVn-FI and rVn-FII promoted cell attachment, although to a lower extent than full-length vitronectin, compared with the BSA control (FIG. 8b). Additionally, rVn-FI induced cell spreading and migration compared with the BSA control, whereas rVn-FII and rVn-FIII induced no cell spreading or migration (FIGS. 8c and 8d). From these results it was confirmed that rVn-FI is the most biologically-active protein among the three recombinant truncations. Additionally, it was also confirmed that rVn-FII exhibited significant cell attachment activity, although this activity was lower than that observed in rVn-FI.

Experimental Example 10. Directed Differentiation from SKPs to Mesenchymal Cells to Osteogenic Cells To isolate SKPs from human foreskin, skin samples composed of epidermis and dermis were dissociated and cultured in a defined medium containing FGF2, EGF, and LIF. Most cells adhered to the culture dishes died within three days, but floating cells formed small spheres. These small spheres were isolated, centrifuged, and separated into single cells with accutase treatment. The single cells were transferred to a new flask 7 days after initial culture. Again, many cells were adhered to each other, but the cells in the floating spheres proliferated to generate larger spheres (FIG. 10a). The spheres were then isolated after 7 days of culture, dissociated, and cultured in fresh medium supplemented with growth factors. Purified populations of floating spheres were obtained after three subcultures over three weeks using this process of selective attachment (FIG. 10a). For each subculture, the spheres were dissociated to single cells and subsequently proliferated to generate new spheres. After the isolation and expansion of the mesenchymal cells from human foreskin, an isolated population of homogeneous human mesenchymal cells was confirmed. The SKP-derived mesenchymal cells were characterized by their ability to proliferate in culture with an attached, well-spread morphology (FIG. 10a) and by the presence of marker proteins on their surfaces (FIG. 10b). These expanded, attached SKP-derived mesenchymal cells were uniformly positive for many surface proteins, including CD29, CD44, CD73, CD133, CD146, and Stro-1 (FIG. 10b). From these results, it was confirmed that human SKPs can differentiate into SKP-derived mesenchymal cells under the described culture conditions.

Osteogenic differentiation was induced in the SKP-derived mesenchymal cell cultures by treatment with β-glycerol phosphate, dexamethasone, and ascorbic acid in the presence of 10% FBS. The differentiated osteogenic cells formed aggregates or nodules, and calcium accumulation was evident after two weeks. Alizarin red S staining suggests that mineral deposits are associated with some of these nodules. These mineral deposits were abundant at two weeks and were localized both to cells in the nodules and to some cells that grew in monolayers (FIG. 10c). qRT-PCR analysis revealed an about 81-fold increase in ALP gene expression compared to SKP-derived mesenchymal cells (FIG. 10d).

Then, the expression of osteogenic-specific markers, including RUNX2, BSP, and osteocalcin, was assessed. As a result, it was confirmed that the expression levels of RUNX2, BSP, and osteocalcin were significantly upregulated in the differentiated osteogenic cells (FIG. 10d). Additionally, upon examination of the expression levels of the osteogenic-specific markers via RT-PCR, it was confirmed that the expression levels of the osteogenic-specific markers were very similar to the results of the qRT-TCR analysis (FIG. 10e). From these results, it was confirmed that SKP-derived mesenchymal cells can differentiate into an osteogenic lineage.

Experimental Example 11. Effects of VnP-16 on F-Actin-Mediated Cytoskeletal Organization in Mature Osteoclasts The osteoclasts were cultured for 1 day on plates precoated with vehicle (DMSO), SP (9.1 µg/cm$^2$), or VnP-16 (9.1 µg/cm$^2$), in the presence of M-CSF (30 ng/mL) and RANKL (100 ng/mL). The cells were observed after immunostaining with DAPI (blue) and rhodamine-phalloidin (red).

As a result, the anti-osteoclastogenic effects of VnP-16 were confirmed by its ability to inhibit F-actin-mediated cytoskeletal organization in preosteoclasts (FIG. 4d) and VnP-16 had no such effect on mature osteoclasts (FIG. 11).

Experimental Example 12. Effects of VnP-16 on Bone Resorbing Activity and Viability of Mature Osteoclasts Mature osteoclasts were cultured for 24 hours on Osteo Assay Surface plates precoated with vehicle (DMSO), SP (9.1 μg/cm$^2$), or VnP-16 (9.1 μg/cm$^2$), in the presence of M-CSF (30 ng/mL) and RANKL (100 ng/mL).

The effect of VnP-16 on the area of resorption pits was examined, and as a result, it was confirmed that the area of the resorption pits observed in osteoclasts cultured for 24 hours is similar to that observed in osteoclasts cultured for 12 hours (FIGS. 12a and 12b). However, it was confirmed that VnP-16 had no effect on the viability of osteoclasts (FIG. 12c).

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for treating bone disease, the method comprising: administering a pharmaceutical composition comprising a peptide for regulating bone formation or bone resorption, which consists of 12 to 173 continuous amino acids within the amino acid sequence of SEQ ID NO: 19 and comprises the amino acid sequence (RVYFFKGKQYWE) of SEQ ID NO: 17, to a subject having bone disease and in need of promoting bone formation or inhibiting bone resorption.

2. The method of claim 1, wherein the bone disease is at least one selected from the group consisting of osteoporosis, Paget's disease, fracture, osteogenesis imperfecta, periodontal disease, and osteoarthritis.

3. A method for treating bone disease, the method comprising: administering a pharmaceutical composition comprising a peptide for regulating bone formation or bone resorption, which consists of the amino acid sequence (RVYFFKGKQYWE) of SEQ ID NO: 17, to a subject having bone disease and in need of promoting bone formation or inhibiting bone resorption.

4. The method of claim 3, wherein the peptide is human vitronectin-derived.

5. The method of claim 3, wherein the peptide has the activity of promoting bone formation.

6. The method of claim 5, wherein the peptide promotes osteoblast differentiation.

7. The method of claim 5, wherein the peptide induces osteoblast differentiation by activating the signaling pathway by focal adhesion kinase (FAK) phosphorylation.

8. The method of claim 3, wherein the peptide has the activity of inhibiting bone resorption.

9. The method of claim 8, wherein the peptide restricts osteoclast differentiation or the bone resorption by inhibiting JNK-c-Fos-NFATc1 signaling pathway.

10. The method of claim 8, wherein the peptide restricts osteoclast differentiation or the bone resorption by inhibiting Src-PYK2 signaling pathway.

11. The method of claim 3, wherein the bone disease is at least one selected from the group consisting of osteoporosis, Paget's disease, fracture, osteogenesis imperfecta, periodontal disease, and osteoarthritis.

\* \* \* \* \*